United States Patent
Hafezi et al.

(10) Patent No.: US 8,945,005 B2
(45) Date of Patent: Feb. 3, 2015

(54) CONTROLLED ACTIVATION INGESTIBLE IDENTIFIER

(75) Inventors: Hooman Hafezi, Redwood City, CA (US); Timothy Robertson, Belmont, CA (US); Olivier Colliou, Los Gatos, CA (US); Mark Zdeblick, Portola Valley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 597 days.

(21) Appl. No.: 12/447,172

(22) PCT Filed: Oct. 25, 2007

(86) PCT No.: PCT/US2007/082563
§ 371 (c)(1),
(2), (4) Date: Apr. 24, 2009

(87) PCT Pub. No.: WO2008/052136
PCT Pub. Date: May 2, 2008

(65) Prior Publication Data
US 2010/0239616 A1   Sep. 23, 2010

Related U.S. Application Data

(60) Provisional application No. 60/862,925, filed on Oct. 25, 2006.

(51) Int. Cl.
*A61K 9/00*   (2006.01)
*A61P 43/00*   (2006.01)
(Continued)

(52) U.S. Cl.
CPC ........... *A61K 49/00* (2013.01); *H01M 10/0436* (2013.01); *A61B 5/6861* (2013.01);
(Continued)

(58) Field of Classification Search
CPC .... A61B 5/073; A61B 5/4839; A61B 5/4848; A61B 5/6871–5/6873; A61B 5/4238; A61B 5/6861; A61B 2560/0214; A61J 3/002–3/10; H01M 4/02–4/0407; H01M 8/08; H01M 2220/10–2220/30; H01M 2300/0002–2300/0005; H01M 10/0436–10/044; H01M 4/86–4/8663; H01M 8/006
USPC ................. 600/300–301, 363–365, 373–374, 600/377–379, 382–384, 386–394, 481, 485, 600/500–503, 509, 515–519, 529–531, 600/544–547, 549; 128/920–925; 705/2–3; 424/400–502
See application file for complete search history.

(56) References Cited

U.S. PATENT DOCUMENTS
3,607,788 A   9/1971   Adolph
3,628,669 A * 12/1971  McKinnis et al. ....... 210/500.21
(Continued)

FOREIGN PATENT DOCUMENTS
CN   1991868   7/2007
CN   101005470  7/2007
(Continued)

OTHER PUBLICATIONS
Hung, L-H et al in "Optimization of Droplet Generation by controlling PDMS surface hydrophibicity", Proceedings of IMECE20042004 ASME International Mechanical Engineering Congress and RD&D Expo, Nov. 13-19, 2004 Anaheim, California, p. 1-2.*
(Continued)

*Primary Examiner* — William Thomson
*Assistant Examiner* — Marie Archer
(74) *Attorney, Agent, or Firm* — K&L Gates LLP

(57) ABSTRACT

Controlled activation identifiers for use in ingestible compositions, such as pharma-informatics enabled compositions, are provided. The identifiers include a controlled activation element that provides for activation of the identifier in response to the presence of a predetermined stimulus at a target site of interest. The invention finds use in a variety of different applications, including but not limited to, monitoring of therapeutic regimen compliance, tracking the history of pharmaceutical agents, etc.

21 Claims, 10 Drawing Sheets

(51) Int. Cl.

| | |
|---|---|
| *H01M 6/32* | (2006.01) |
| *A61K 49/00* | (2006.01) |
| *H01M 10/04* | (2006.01) |
| *A61B 5/07* | (2006.01) |
| *A61B 5/145* | (2006.01) |
| *A61B 5/1473* | (2006.01) |
| *A61B 5/00* | (2006.01) |
| *H01M 10/00* | (2006.01) |
| *A61J 3/00* | (2006.01) |

(52) U.S. Cl.
CPC .............. *A61B5/4238* (2013.01); *A61B 5/073* (2013.01); *A61B 5/14539* (2013.01); *A61B 5/1473* (2013.01); *A61B 5/4839* (2013.01); *A61B 2560/0214* (2013.01); *A61J 3/007* (2013.01)
USPC ........ 600/300; 600/302; 340/572.1; 429/498; 424/408

(56) References Cited

U.S. PATENT DOCUMENTS

| | | | |
|---|---|---|---|
| 3,642,008 A | 2/1972 | Bolduc | |
| 3,679,480 A | 7/1972 | Brown et al. | |
| 3,682,160 A | 8/1972 | Murata | |
| 3,719,183 A | 3/1973 | Schwartz | |
| 3,828,766 A | 8/1974 | Krasnow | |
| 3,837,339 A | 9/1974 | Aisenberg et al. | |
| 3,893,111 A | 7/1975 | Cotter | |
| 3,944,064 A | 3/1976 | Bashaw et al. | |
| 3,967,202 A | 6/1976 | Batz | |
| 3,989,050 A | 11/1976 | Buchalter | |
| 4,017,856 A | 4/1977 | Wiegand | |
| 4,055,178 A | 10/1977 | Harrigan | |
| 4,062,750 A | 12/1977 | Butler | |
| 4,077,397 A | 3/1978 | Ellis | |
| 4,077,398 A | 3/1978 | Ellis | |
| 4,082,087 A | 4/1978 | Howson | |
| 4,090,752 A | 5/1978 | Long | |
| 4,106,348 A | 8/1978 | Auphan | |
| 4,129,125 A | 12/1978 | Lester | |
| 4,166,453 A | 9/1979 | McClelland | |
| 4,239,046 A | 12/1980 | Ong | |
| 4,251,795 A | 2/1981 | Shibasaki et al. | |
| 4,269,189 A | 5/1981 | Abraham | |
| 4,331,654 A | 5/1982 | Morris | |
| 4,345,588 A | 8/1982 | Widder et al. | |
| 4,418,697 A | 12/1983 | Tama | |
| 4,425,117 A | 1/1984 | Hugemann et al. | |
| 4,439,196 A | 3/1984 | Higuchi | |
| 4,494,950 A | 1/1985 | Fischell | |
| 4,559,950 A | 12/1985 | Vaughan | |
| 4,564,363 A | 1/1986 | Bagnall et al. | |
| 4,635,641 A | 1/1987 | Hoffman | |
| 4,654,165 A | 3/1987 | Eisenberg | |
| 4,669,479 A | 6/1987 | Dunseath | |
| 4,687,660 A | 8/1987 | Baker et al. | |
| 4,725,997 A | 2/1988 | Urquhart et al. | |
| 4,763,659 A | 8/1988 | Dunseath | |
| 4,784,162 A | 11/1988 | Ricks | |
| 4,793,825 A | 12/1988 | Benjamin et al. | |
| 4,809,705 A | 3/1989 | Ascher | |
| 4,844,076 A | 7/1989 | Lesho | |
| 4,876,093 A | 10/1989 | Theeuwes et al. | |
| 4,896,261 A | 1/1990 | Nolan | |
| 4,975,230 A | 12/1990 | Pinkhasov | |
| 4,987,897 A | 1/1991 | Funke | |
| 5,000,957 A | 3/1991 | Eckenhoff et al. | |
| 5,016,634 A | 5/1991 | Vock | |
| 5,079,006 A | 1/1992 | Urquhart | |
| 5,167,626 A | 12/1992 | Casper | |
| 5,176,626 A | 1/1993 | Soehendra | |
| 5,245,332 A | 9/1993 | Katzenstein et al. | |
| 5,261,402 A | 11/1993 | DiSabito | |
| 5,263,481 A | 11/1993 | Axelgaard et al. | |
| 5,279,607 A | 1/1994 | Schentag et al. | |
| 5,281,287 A | 1/1994 | Lloyd | |
| 5,283,136 A | 2/1994 | Peled et al. | |
| 5,305,745 A | 4/1994 | Zacouto | |
| 5,318,557 A | 6/1994 | Gross | |
| 5,394,882 A | 3/1995 | Mawhinney | |
| 5,395,366 A | 3/1995 | D'Andrea et al. | |
| 5,458,141 A | 10/1995 | Neil et al. | |
| 5,485,841 A | 1/1996 | Watkin et al. | |
| 5,511,548 A | 4/1996 | Riazzi et al. | |
| 5,567,210 A | 10/1996 | Bates et al. | |
| 5,596,302 A | 1/1997 | Mastrocola et al. | |
| D377,983 S | 2/1997 | Sabri et al. | |
| 5,600,548 A | 2/1997 | Nguyen et al. | |
| 5,634,468 A | 6/1997 | Platt | |
| 5,645,063 A | 7/1997 | Straka | |
| 5,720,771 A | 2/1998 | Snell | |
| 5,738,708 A | 4/1998 | Peachey et al. | |
| 5,740,811 A | 4/1998 | Hedberg | |
| 5,757,326 A | 5/1998 | Koyama et al. | |
| 5,792,048 A | 8/1998 | Schaefer | |
| 5,802,467 A | 9/1998 | Salazar | |
| 5,833,716 A | 11/1998 | Bar-Or | |
| 5,845,265 A | 12/1998 | Woolston | |
| 5,862,803 A | 1/1999 | Besson | |
| 5,868,136 A | 2/1999 | Fox | |
| 5,921,925 A | 7/1999 | Cartmell et al. | |
| 5,925,030 A | 7/1999 | Gross et al. | |
| 5,957,854 A | 9/1999 | Besson | |
| 5,963,132 A | 10/1999 | Yoakum et al. | |
| 5,974,124 A | 10/1999 | Schlueter, Jr. et al. | |
| 5,999,846 A | 12/1999 | Pardey et al. | |
| 6,023,631 A | 2/2000 | Cartmell et al. | |
| 6,038,464 A | 3/2000 | Axelgaard et al. | |
| 6,042,710 A | 3/2000 | Dubrow | |
| 6,047,203 A | 4/2000 | Sackner | |
| 6,076,016 A | 6/2000 | Feierbach et al. | |
| 6,081,734 A | 6/2000 | Batz | |
| 6,083,248 A | 7/2000 | Thompson | |
| 6,090,489 A * | 7/2000 | Hayakawa et al. ........... 428/409 |
| 6,095,985 A | 8/2000 | Raymond et al. | |
| 6,117,077 A | 9/2000 | Del Mar et al. | |
| 6,122,351 A | 9/2000 | Schlueter, Jr. et al. | |
| 6,141,592 A | 10/2000 | Pauly | |
| 6,149,940 A | 11/2000 | Maggi et al. | |
| 6,200,265 B1 | 3/2001 | Walsh et al. | |
| 6,204,764 B1 | 3/2001 | Maloney | |
| 6,206,702 B1 | 3/2001 | Hayden et al. | |
| 6,217,744 B1 | 4/2001 | Crosby | |
| 6,231,593 B1 | 5/2001 | Meserol | |
| 6,245,057 B1 | 6/2001 | Sieben et al. | |
| 6,269,058 B1 | 7/2001 | Yamanoi et al. | |
| 6,275,476 B1 | 8/2001 | Wood | |
| 6,285,897 B1 | 9/2001 | Kilcoyne et al. | |
| 6,287,252 B1 | 9/2001 | Lugo | |
| 6,288,629 B1 | 9/2001 | Cofino et al. | |
| 6,289,238 B1 | 9/2001 | Besson | |
| 6,315,719 B1 | 11/2001 | Rode et al. | |
| 6,342,774 B1 | 1/2002 | Kreisinger et al. | |
| 6,344,824 B1 | 2/2002 | Takasugi et al. | |
| 6,358,202 B1 | 3/2002 | Arent | |
| 6,364,834 B1 | 4/2002 | Reuss | |
| 6,366,206 B1 | 4/2002 | Ishikawa et al. | |
| 6,368,190 B1 | 4/2002 | Easter et al. | |
| 6,371,927 B1 | 4/2002 | Brune | |
| 6,374,670 B1 | 4/2002 | Spelman | |
| 6,380,858 B1 | 4/2002 | Yarin et al. | |
| 6,390,088 B1 | 5/2002 | Noehl et al. | |
| 6,394,953 B1 | 5/2002 | Devlin et al. | |
| 6,394,997 B1 | 5/2002 | Lemelson | |
| 6,409,674 B1 | 6/2002 | Brockway et al. | |
| 6,426,863 B1 | 7/2002 | Munshi | |
| 6,432,292 B1 | 8/2002 | Pinto et al. | |
| 6,440,069 B1 | 8/2002 | Raymond et al. | |
| 6,441,747 B1 | 8/2002 | Khair | |
| 6,453,199 B1 | 9/2002 | Kobozev | |
| 6,477,424 B1 | 11/2002 | Thompson et al. | |
| 6,482,156 B2 | 11/2002 | Lliff | |

(56) References Cited

U.S. PATENT DOCUMENTS

| | | |
|---|---|---|
| 6,496,705 B1 | 12/2002 | Ng et al. |
| 6,526,315 B1 | 2/2003 | Inagawa |
| 6,544,174 B2 | 4/2003 | West |
| 6,564,079 B1 | 5/2003 | Cory |
| 6,577,893 B1 | 6/2003 | Besson |
| 6,579,231 B1 | 6/2003 | Phipps |
| 6,599,284 B2 | 7/2003 | Faour et al. |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino et al. |
| 6,757,523 B2 | 6/2004 | Fry |
| 6,759,968 B2 | 7/2004 | Zierolf |
| 6,773,429 B2 | 8/2004 | Sheppard et al. |
| 6,800,060 B2 | 10/2004 | Marshall |
| 6,801,137 B2 | 10/2004 | Eggers et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | von Alten |
| 6,937,150 B2 | 8/2005 | Medema |
| 6,942,616 B2 | 9/2005 | Kerr |
| 6,951,536 B2 | 10/2005 | Yokoi |
| 6,957,107 B2 | 10/2005 | Rogers et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,076,437 B1 | 7/2006 | Levy |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard |
| 7,349,722 B2 | 3/2008 | Witkowski |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,471,665 B2 | 12/2008 | Perlman |
| 7,499,674 B2 | 3/2009 | Salokannel |
| 7,502,643 B2 | 3/2009 | Farringdon et al. |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,558,620 B2 | 7/2009 | Ishibashi |
| 7,575,005 B2 | 8/2009 | Mumford |
| 7,616,111 B2 | 11/2009 | Covannon |
| 7,616,710 B2 | 11/2009 | Kim et al. |
| 7,617,001 B2 | 11/2009 | Penner |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |

(56) References Cited

U.S. PATENT DOCUMENTS

| | | |
|---|---|---|
| 7,673,679 B2 | 3/2010 | Harrison et al. |
| 7,678,043 B2 | 3/2010 | Gilad |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,779,614 B1 | 8/2010 | McGonagle et al. |
| 7,796,043 B2 | 9/2010 | Euliano et al. |
| 7,797,033 B2 | 9/2010 | D'Andrea et al. |
| 7,806,852 B1 | 10/2010 | Jursen |
| 7,809,399 B2 | 10/2010 | Lu |
| 7,844,341 B2 | 11/2010 | Von Arx et al. |
| 7,904,133 B2 | 3/2011 | Gehman et al. |
| D639,437 S | 6/2011 | Bishay et al. |
| 8,025,149 B2 | 9/2011 | Sterry et al. |
| 8,036,731 B2 | 10/2011 | Kimchy et al. |
| 8,073,707 B2 | 12/2011 | Teller et al. |
| 8,083,128 B2 | 12/2011 | Dembo et al. |
| 8,123,576 B2 | 2/2012 | Kim |
| 8,180,425 B2 | 5/2012 | Selvitelli et al. |
| 8,200,320 B2 | 6/2012 | Kovacs |
| 8,214,007 B2 | 7/2012 | Baker et al. |
| 8,224,667 B1 | 7/2012 | Miller et al. |
| 8,238,998 B2 | 8/2012 | Park |
| 8,249,686 B2 | 8/2012 | Libbus et al. |
| 8,258,962 B2 | 9/2012 | Robertson et al. |
| 8,285,356 B2 | 10/2012 | Bly et al. |
| 8,290,574 B2 | 10/2012 | Feild et al. |
| 8,301,232 B2 | 10/2012 | Albert et al. |
| 8,308,640 B2 | 11/2012 | Baldus et al. |
| 8,315,687 B2 | 11/2012 | Cross et al. |
| 8,369,936 B2 | 2/2013 | Farringdon et al. |
| 8,386,009 B2 | 2/2013 | Lindberg et al. |
| 8,389,003 B2 | 3/2013 | Mintchev et al. |
| 8,440,274 B2 | 5/2013 | Wang |
| 8,597,186 B2 | 12/2013 | Hafezi et al. |
| 2001/0027331 A1 | 10/2001 | Thompson |
| 2001/0031071 A1 | 10/2001 | Nichols et al. |
| 2001/0044588 A1 | 11/2001 | Mault |
| 2001/0051766 A1 | 12/2001 | Gazdzinski |
| 2001/0056262 A1 | 12/2001 | Cabiri et al. |
| 2002/0002326 A1 | 1/2002 | Causey, III |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0138009 A1 | 9/2002 | Brockway et al. |
| 2002/0193669 A1 | 12/2002 | Glukhovsky |
| 2002/0193846 A1 | 12/2002 | Pool et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0063522 A1 | 4/2003 | Sagar |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0229382 A1 | 12/2003 | Sun et al. |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0111011 A1 | 6/2004 | Uchiyama et al. |
| 2004/0115517 A1 | 6/2004 | Fukuda et al. |
| 2004/0121015 A1 | 6/2004 | Chidlaw et al. |
| 2004/0122297 A1 | 6/2004 | Stahmann et al. |
| 2004/0148140 A1 | 7/2004 | Tarassenko et al. |
| 2004/0153007 A1 | 8/2004 | Harris |
| 2004/0167226 A1 | 8/2004 | Serafini et al. |
| 2004/0167801 A1 | 8/2004 | Say et al. |
| 2004/0171914 A1 | 9/2004 | Avni |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0260154 A1 | 12/2004 | Sidelnik |
| 2004/0267240 A1 | 12/2004 | Gross et al. |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0151625 A1 | 7/2005 | Lai |
| 2005/0154428 A1 | 7/2005 | Bruinsma |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |

(56) References Cited

U.S. PATENT DOCUMENTS

| | | |
|---|---|---|
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0280539 A1 | 12/2005 | Pettus |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0247505 A1 | 11/2006 | Siddiqui |
| 2006/0253005 A1 | 11/2006 | Drinan |
| 2006/0255064 A1 | 11/2006 | Donaldson |
| 2006/0265246 A1 | 11/2006 | Hoag |
| 2006/0267774 A1* | 11/2006 | Feinberg et al. ............ 340/572.8 |
| 2006/0270346 A1 | 11/2006 | Ibrahim |
| 2006/0273882 A1 | 12/2006 | Posamentier |
| 2006/0276702 A1* | 12/2006 | McGinnis .................... 600/372 |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0066929 A1 | 3/2007 | Ferren et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0180047 A1 | 8/2007 | Dong et al. |
| 2007/0184115 A1* | 8/2007 | Mamajiwalla et al. ........ 424/486 |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0014866 A1 | 1/2008 | Lipowski |
| 2008/0015421 A1 | 1/2008 | Penner |
| 2008/0015494 A1 | 1/2008 | Santini et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0033301 A1 | 2/2008 | Dellavecchia et al. |
| 2008/0038588 A1 | 2/2008 | Lee |
| 2008/0039700 A1 | 2/2008 | Drinan et al. |
| 2008/0046038 A1 | 2/2008 | Hill |
| 2008/0051647 A1* | 2/2008 | Wu et al. ..................... 600/382 |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemiec et al. |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |

(56) References Cited

U.S. PATENT DOCUMENTS

| | | |
|---|---|---|
| 2008/0188837 A1 | 8/2008 | Belsky |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0223936 A1 | 9/2008 | Mickle et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0306362 A1 | 12/2008 | Davis |
| 2008/0311852 A1 | 12/2008 | Hansen |
| 2008/0312522 A1 | 12/2008 | Rowlandson |
| 2008/0316020 A1 | 12/2008 | Robertson |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076397 A1 | 3/2009 | Libbus et al. |
| 2009/0082645 A1 | 3/2009 | Hafezi et al. |
| 2009/0087483 A1 | 4/2009 | Sison |
| 2009/0088618 A1 | 4/2009 | Ameson |
| 2009/0099435 A1 | 4/2009 | Say et al. |
| 2009/0105561 A1 | 4/2009 | Boyden et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0142853 A1 | 6/2009 | Warrington et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl et al. |
| 2009/0281539 A1 | 11/2009 | Selig |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0006585 A1 | 1/2010 | Flowers et al. |
| 2010/0010330 A1 | 1/2010 | Rankers |
| 2010/0033324 A1 | 2/2010 | Shimizu et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |

(56) References Cited

U.S. PATENT DOCUMENTS

| | | | |
|---|---|---|---|
| 2010/0063438 A1 | 3/2010 | Bengtsson | |
| 2010/0063841 A1 | 3/2010 | D'Ambrosia et al. | |
| 2010/0069002 A1 | 3/2010 | Rong | |
| 2010/0069717 A1 | 3/2010 | Hafezi et al. | |
| 2010/0081894 A1 | 4/2010 | Zdeblick et al. | |
| 2010/0099967 A1 | 4/2010 | Say et al. | |
| 2010/0099968 A1 | 4/2010 | Say et al. | |
| 2010/0099969 A1 | 4/2010 | Say et al. | |
| 2010/0100077 A1 | 4/2010 | Rush | |
| 2010/0100078 A1 | 4/2010 | Say et al. | |
| 2010/0106001 A1 | 4/2010 | Say et al. | |
| 2010/0118853 A1 | 5/2010 | Godfrey | |
| 2010/0139672 A1 | 6/2010 | Kroll et al. | |
| 2010/0160742 A1 | 6/2010 | Seidl et al. | |
| 2010/0168659 A1 | 7/2010 | Say et al. | |
| 2010/0179398 A1 | 7/2010 | Say et al. | |
| 2010/0185055 A1 | 7/2010 | Robertson | |
| 2010/0191073 A1 | 7/2010 | Tarassenko et al. | |
| 2010/0210299 A1 | 8/2010 | Gorbachov | |
| 2010/0222652 A1 | 9/2010 | Cho | |
| 2010/0228113 A1 | 9/2010 | Solosko | |
| 2010/0233026 A1 | 9/2010 | Ismagliov et al. | |
| 2010/0234706 A1 | 9/2010 | Gilland | |
| 2010/0234715 A1 | 9/2010 | Shin | |
| 2010/0234914 A1 | 9/2010 | Shen | |
| 2010/0245091 A1 | 9/2010 | Singh | |
| 2010/0249881 A1 | 9/2010 | Corndorf | |
| 2010/0256461 A1 | 10/2010 | Mohamedali | |
| 2010/0259543 A1 | 10/2010 | Tarassenko et al. | |
| 2010/0268048 A1 | 10/2010 | Say et al. | |
| 2010/0268049 A1 | 10/2010 | Say et al. | |
| 2010/0268050 A1 | 10/2010 | Say et al. | |
| 2010/0274111 A1 | 10/2010 | Say et al. | |
| 2010/0280345 A1 | 11/2010 | Say et al. | |
| 2010/0280346 A1 | 11/2010 | Say et al. | |
| 2010/0295694 A1 | 11/2010 | Kauffman et al. | |
| 2010/0298668 A1 | 11/2010 | Hafezi et al. | |
| 2010/0298730 A1 | 11/2010 | Tarassenko et al. | |
| 2010/0299155 A1 | 11/2010 | Findlay et al. | |
| 2010/0312188 A1 | 12/2010 | Robertson et al. | |
| 2010/0312580 A1 | 12/2010 | Tarassenko et al. | |
| 2010/0332443 A1 | 12/2010 | Gartenberg | |
| 2011/0004079 A1 | 1/2011 | Al-Ali et al. | |
| 2011/0009715 A1 | 1/2011 | O'Reilly et al. | |
| 2011/0040203 A1 | 2/2011 | Savage et al. | |
| 2011/0050431 A1 | 3/2011 | Hood et al. | |
| 2011/0054265 A1 | 3/2011 | Hafezi et al. | |
| 2011/0065983 A1 | 3/2011 | Hafezi et al. | |
| 2011/0077660 A1* | 3/2011 | Janik et al. | 606/129 |
| 2011/0081860 A1 | 4/2011 | Brown et al. | |
| 2011/0105864 A1 | 5/2011 | Robertson et al. | |
| 2011/0144470 A1 | 6/2011 | Mazar et al. | |
| 2011/0237924 A1 | 9/2011 | McGusty et al. | |
| 2011/0279963 A1 | 11/2011 | Kumar et al. | |
| 2012/0024889 A1 | 2/2012 | Robertson et al. | |
| 2012/0029309 A1 | 2/2012 | Paquet et al. | |
| 2012/0083715 A1 | 4/2012 | Yuen et al. | |
| 2012/0089000 A1 | 4/2012 | Bishay et al. | |
| 2012/0101396 A1 | 4/2012 | Solosko et al. | |
| 2012/0197144 A1 | 8/2012 | Christ et al. | |
| 2012/0214140 A1 | 8/2012 | Brynelsen et al. | |
| 2012/0265544 A1 | 10/2012 | Hwang et al. | |
| 2012/0299723 A1 | 11/2012 | Hafezi et al. | |
| 2012/0310070 A1 | 12/2012 | Kumar et al. | |
| 2012/0316413 A1 | 12/2012 | Liu et al. | |
| 2013/0030259 A1 | 1/2013 | Thomsen et al. | |
| 2013/0057385 A1 | 3/2013 | Murakami et al. | |
| 2013/0060115 A1 | 3/2013 | Gehman et al. | |

FOREIGN PATENT DOCUMENTS

| | | |
|---|---|---|
| CN | 201076456 | 6/2008 |
| EP | 0344939 | 12/1989 |
| EP | 1246356 | 10/2002 |
| EP | 1534054 | 5/2005 |
| EP | 1702553 | 9/2006 |
| EP | 1789128 | 5/2007 |
| EP | 2143369 | 1/2010 |
| GB | 2432862 | 6/2007 |
| IL | 172917 | 6/2010 |
| JP | 61017949 | 1/1986 |
| JP | 61072712 | 4/1986 |
| JP | 05-228128 | 9/1993 |
| JP | H0646539 | 2/1994 |
| JP | 09-330159 | 12/1997 |
| JP | 10-14898 | 1/1998 |
| JP | 2000-506410 | 5/2000 |
| JP | 2002-224053 | 8/2002 |
| JP | 2002263185 | 9/2002 |
| JP | 2002291684 | 10/2002 |
| JP | 2004-7187 | 1/2004 |
| JP | 2004134384 | 4/2004 |
| JP | 2004-313242 | 11/2004 |
| JP | 2005-073886 | 3/2005 |
| JP | 2005-304880 | 4/2005 |
| JP | 2005124708 | 5/2005 |
| JP | 2005-532841 | 11/2005 |
| JP | 2005-532849 | 11/2005 |
| JP | 2006006377 | 1/2006 |
| JP | 2006509574 | 3/2006 |
| JP | 2006-177699 | 7/2006 |
| JP | 2006-187611 | 7/2006 |
| JP | 2006278091 | 10/2006 |
| JP | 2006346000 | 12/2006 |
| JP | 2007159631 | 6/2007 |
| JP | 2007-313340 | 12/2007 |
| JP | 2008011865 | 1/2008 |
| JP | 2008501415 | 1/2008 |
| JP | 2009-061236 | 3/2009 |
| KR | 20020015907 | 3/2002 |
| KR | 20020061744 | 7/2002 |
| KR | 200609977523 | 7/2006 |
| KR | 927471 | 11/2009 |
| KR | 10-2012-09995 | 9/2012 |
| TW | 553735 | 9/2003 |
| TW | 200724094 | 7/2007 |
| WO | 8802237 | 4/1988 |
| WO | WO8802237 | 4/1988 |
| WO | WO9308734 | 5/1993 |
| WO | WO9319667 | 10/1993 |
| WO | WO9401165 | 1/1994 |
| WO | WO9714112 | 4/1997 |
| WO | WO9739963 | 10/1997 |
| WO | WO9843537 | 10/1998 |
| WO | WO9937290 | 7/1999 |
| WO | WO9959465 | 11/1999 |
| WO | WO0033246 | 6/2000 |
| WO | WO0100085 | 1/2001 |
| WO | 01/47466 | 7/2001 |
| WO | WO0149364 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO02095351 | 11/2002 |
| WO | WO03005877 | 1/2003 |
| WO | WO03050643 | 6/2003 |
| WO | WO03068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2005011237 | 2/2005 |
| WO | 2005/020023 | 3/2005 |

(56) References Cited

FOREIGN PATENT DOCUMENTS

| | | |
|---|---|---|
| WO | WO2005024687 | 3/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005082436 | 9/2005 |
| WO | WO2005083621 | 9/2005 |
| WO | WO2005110238 | 11/2005 |
| WO | WO2006021932 | 3/2006 |
| WO | WO2006027586 | 3/2006 |
| WO | WO2006028347 | 3/2006 |
| WO | WO 2006028347 A1 * | 3/2006 |
| WO | WO2006035351 | 4/2006 |
| WO | 2006/055892 | 5/2006 |
| WO | 2006/055956 | 5/2006 |
| WO | WO2006046648 | 5/2006 |
| WO | WO2006075016 | 7/2006 |
| WO | WO2006100620 | 9/2006 |
| WO | 2006/104843 | 10/2006 |
| WO | WO2006109072 | 10/2006 |
| WO | 2006/116718 | 11/2006 |
| WO | 2006/127355 | 11/2006 |
| WO | WO2006119345 | 11/2006 |
| WO | 2007/001724 | 1/2007 |
| WO | 2007/001742 | 1/2007 |
| WO | 2007/013952 | 2/2007 |
| WO | 2007/014084 | 2/2007 |
| WO | 2007/021496 | 2/2007 |
| WO | WO2007014527 | 2/2007 |
| WO | 2007/027660 | 3/2007 |
| WO | 2007/028035 | 3/2007 |
| WO | WO2007028035 | 3/2007 |
| WO | 2007036741 | 4/2007 |
| WO | 2007036746 | 4/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | 2007130491 | 11/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007133526 | 11/2007 |
| WO | 2007/149546 | 12/2007 |
| WO | WO2007143535 | 12/2007 |
| WO | 2008/008281 | 1/2008 |
| WO | WO2008012700 | 1/2008 |
| WO | WO2008030482 | 3/2008 |
| WO | 2008/052136 | 5/2008 |
| WO | 2008/063626 | 5/2008 |
| WO | WO2008061138 | 5/2008 |
| WO | 2008/066617 | 6/2008 |
| WO | WO2008076464 | 6/2008 |
| WO | WO2008089232 | 7/2008 |
| WO | WO2008091683 | 7/2008 |
| WO | 2008/095183 | 8/2008 |
| WO | 2008/101107 | 8/2008 |
| WO | WO2008097652 | 8/2008 |
| WO | 2008/112577 | 9/2008 |
| WO | 2008/112578 | 9/2008 |
| WO | 2008120156 | 10/2008 |
| WO | WO2008133394 | 11/2008 |
| WO | WO2008134185 | 11/2008 |
| WO | 2009001108 | 12/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | 2010019778 | 2/2010 |
| WO | 2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010115194 | 10/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |
| WO | WO2013012869 | 1/2013 |

OTHER PUBLICATIONS

Rolison, D. R. et al., "Electrically conductive oxide aerogels: new materials in electrochemistry", J. Mater. Chem., 2001, 11, 963-980.*

Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.*

"Smartlife awarded patent for knitted transducer" Innovation in Textiles News: http://www.innovationintextiles.com/articles/208.php; 2pp. (2009).

Mackay et al., Radio telemetering from within the body: Inside information is revealed by tiny transmitters that can be swallowed or implanted in man or animal. Science 1961;134(3486):1196-1202.

Mackay et al,. Endoradiosonde. Nature 1957;179(4572):1239-40, 179.

Zworkin, A 'radio pill.' Nature 1957;179:898.

Yao et al., Low Power Digital Communication in Implantable Devices Using Volume Conduction of Biological Tissues. Proceedings of the 28th IEEE, EMBC Annual International Conference 2006 (Aug. 30-Sep. 3); New York, USA.

Mckenzie et al., Validation of a new telemetric core temperature monitor. J. Therm. Biol. 2004;29(7-8):605-11.

Tatbul et al., Confidence-based data management for personal area sensor networks. ACM International Conference Proceeding Series 2004;72.

Zimmerman, Personal Area Networks: Near-field intrabody communication. IBM Systems Journal 1996;35 (3-4):609-17.

Mini Mitter Co, Inc. 510(k) Premarket Notification Mini-Logger for Diagnostic Spirometer. Sep. 21, 1999.

Philips Respironics. 510(k) Premarket Notification for VitalSense. Apr. 22, 2004.

Mini Mitter Co, Inc. Actiheart. Traditional 510(k) Summary. Sep. 27, 2005.

Mini Mitter Co, Inc. VitalSense Integrated Physiological Monitoring System. Product Description.

Mini Mitter Co, Inc. VitalSense—Wireless Vital Signs Monitoring. Temperatures.com Mar. 31, 2009.

Mini Mitter Co, Inc. Noninvasive technology to help your studies succeed. Mini Mitter.com Mar. 31, 2009.

Barrie, Heidelberg pH capsule gastric analysis. Textbook of Natural Medicine, 1992, Pizzorno, Murray & Barrie.

Carlson et al., Evaluation of a non-invasive respiratory monitoring system for sleeping subjects. Physiological Measurement 1999;20(1):53.

(56) References Cited

OTHER PUBLICATIONS

Mojaverian et al., Estimation of gastric residence time of the Heidelberg capsule in humans: effect of varying food composition. Gastroenterology 1985;89(2):392-7.

Xiaoming et al., A telemedicine system for wireless home healthcare based on bluetooth and the internet. Telemedicine Journal and e-health 2004;10(S2):S110-6.

Arshak et al., A Review and Adaptation of Methods of Object Tracking to Telemetry Capsules IC-Med (2007) vol. 1, No. 1, Issue 1, pp. 35 of 46.

"ASGE Technology Status Evaluation Report: wireless capsule endoscopy" American Soc. for Gastrointestinal Endoscopy (2006) vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; (2003); abstract.

Brock, "Smart Medicine: The Application of Auto-ID Technology to Healthcare" Auto-ID Labs (2002) http://www.autoidlabs.org/uploads/media/MIT-AUTOID-WH-010.pdf.

Delvaux et al., "Capsule endoscopy: Technique and indications" Clinical Gastoenterology (2008) vol. 22, Issue 5, pp. 813-837.

Fawaz et al., "Enhanced Telemetry System using CP-QPSK Band-Pass Modulation Technique Suitable for Smart Pill Medical Application" IFIP IEEE Dubai Conference (N.D.); http://www.asic.fh-offenburg.de/downloads/ePille/IFIP_IEEE_Dubai_Conference.pdf.

Given Imaging, "Agile Patency Brochure" http://www.inclino.no/documents/AgilePatencyBrochure_Global_GMB-0118-01.pdf;(N.D.) 4pp.

Gonzalez-Guillaumin et al., "Ingestible capsule for impedance and pH monitoring in the esophagus" IEEE Trans Biomed Eng. (2007) 54(12: 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Melanson, "Walkers swallow RFID pills for science" Engadget (2008); http://www.engadget.com/2008/07/29/walkers-swallow-rfid-pills-for-science/.

"New 'smart pill' to track adherence" E-Health-Insider (2010) http://www.e-health-insider.com/news/5910/new_'smart_pill'_monitors_medicines.

"RFID "pill" monitors marchers" RFID News (2008) http://www.rfidnews.org/2008/07/23/rfid-pill-monitors-marchers/.

"SensiVida minimally invasive clinical systems" Investor Presentation Oct. 2009 28pp; http://www.sensividamedtech.com/SensiVidaGeneralOctober09.pdf.

Shrivas et al., "A New Platform for Bioelectronics-Electronic Pill", Cummins College, N.D.; http://www.cumminscollege.org/downloads/electronics_and_telecommunication/Newsletters/Current%20Newsletters.pdf.

"The SmartPill Wireless Motility Capsule" SmartPill, The Measure of GI Health; http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Swedberg, "University Team Sees Ingestible RFID Tag as a Boon to Clinical Trials" RFID Journal Apr. 27, 2010; http://www.rfidjournal.com/article/view/7560/1.

University of Florida News "Rx for health: Engineers design pill that signals it has been swallowed" (2010) 2pp.; http://news.ufl.edu/2010/03/31/antenna-pill-2/.

Intromedic, MiroCam Innovative Capsule Endoscope Pamphlet. 8 pages. (http://www.intromedic.com/en/product/productInfo.asp).

Mini Mitter Co, Inc. 510(k) Premarket Notification for VitalSense. Apr. 22, 2004.

Hotz "The Really Smart Phone" The Wall Street Journal, What They Know (2011); 6 pp.

ISFET—Ion Sensitive Field-Effect Transistor; Microsens S.A. pdf document. pp. 1-4.

Walkey, "MOSFET Struture and Processing"; 97.398* Physical Electronics Lecture 20; pp. 1-24.

Description of ePatch Technology Platform for ECG and EMG, located it http://www.madebydelta.com/imported/images/DELTA_Web/documents/ME/ePatch_ECG_EMG.pdf, Dated Sep. 2, 2010.

Coury, L. "Conductance Measurement Part 1: Theory"; Current Separations, 18:3 (1999) p. 91-96.

Watson, et al., "Determination of the relationship between the pH and conductivity of gastric juice" Physiol Meas. 17 (1996) pp. 21-27.

Gilson, D.R. "Molecular dynamics simulation of dipole interactions", Department of Physics, Hull University, Dec. 2002, p. 1-43.

Li, P-Y, et al. "An electrochemical intraocular drug delivery device", Sensors and Actuators A 143 (2008) p. 41-48.

NPL_AntennaBasics.pdf, p. 1-3.

Santini, J.T. et al, "Microchips as controlled drug delivery-devices", Agnew. Chem. Int. Ed. 2000, vol. 39, p. 2396-2407.

Shawgo, R.S. et al. "BioMEMS from drug delivery", Current Opinion in Solid State and Material Science 6 (2002), p. 329-334.

Soper, S.A. et al. "Bio-Mems Technologies and Applications", Chapter 12, "MEMS for Drug Delivery", p. 325-346.

Tierney, M.J. et al "Electroreleasing Composite Membranes for Delivery of Insulin and other Biomacromolecules", J. Electrochem. Soc., vol. 137, No. 6, Jun. 1990, p. 2005-2006.

Heydari et al., "Analysis of the PLL jitter due to power/ground and substrate noise"; IEEE Transactions on Circuits and Systems (2004) 51(12): 2404-16.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Yang et al., "Fast-switching frequency synthesizer with a discriminator-aided phase detector" IEEE Journal of Solid-State Circuits (2000) 35(10): 1445-52.

Bohidar et al., "Dielectric Behavior of Gelatin Solutions and Gels" Colloid Polym Sci (1998) 276:81-86.

Dhar et al., "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

Ferguson et al., "Dialectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Given Imaging, "Agile Patency Brochure" (2006) http://www.inclino.no/documents/AgilePatencyBrochure_Global_GMB-0118-01.pdf; 4pp.

ISFET—Ion Sensitive Field-Effect Transistor; Microsens S.A. pdf document. First cited by Examiner in Office Action dated Jun. 13, 2011 for U.S. Appl. No. 12/238,345; 4pp.

Intromedic, MicroCam Innovative Capsule Endoscope Pamphlet. (2006) 8 pp (http://www.intromedic.com/en/product/productinfo.asp).

Kamada K., "Electrophoretic deposition assisted by soluble anode" Materials Letters 57 (2003) 2348-2351.

NPL_AntennaBasics.pdf, Radio Antennae, http://www.erikdeman.de/html/sail018h.htm; (2008) 3pp.

O'Brien et al., "The Production and Characterization of Chemically Reactive Porous Coatings of Zirconium Via Unbalanced Magnetron Sputtering" Surface and Coatings Technology (1996) 86-87; 200-206.

Roulstone, et al., "Studies on Polymer Latex Films: I. A study of latex film morphology" Polymer International 24 (1991) pp. 87-94.

Shin et al., "A Simple Route to Metal Nanodots and Nanoporous Metal Films"; Nano Letters, vol. 2, No. 9 (2002) pp. 933-936.

Soper, S.A. et al. "Bio-Mems Technologies and Applications", Chapter 12, "MEMS for Drug Delivery", p. 325-346 (2007).

(56) References Cited

OTHER PUBLICATIONS

U.S. Appl. No. 12/238,345, filed Sep. 25, 2008, Hooman et al., Non-Final Office Action mailed Jun. 13, 2011 22pp.

Walkey, "MOSFET Structure and Processing"; 97.398* Physical Electronics Lecture 20; First cited by Examiner in Office Action dated Jun. 13, 2011 for U.S. Appl. No. 12/238,345; 24 pp.

Wongmanerod et al., "Determination of pore size distribution and surface area of thin porous silicon layers by spectroscopic ellipsometry" Applied Surface Science 172 (2001) 117-125.

"PALO Bluetooth Baseband" PALO Bluetooth Resource Center (2002) Retrieved from internet Dec. 12, 2012 at URL:http://palowireless.com/bluearticles/baseband.asp; first cited in Office Action dated Jan. 17, 2013 for EP08853901.0.

Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.

Lin et al., "Do Physiological Data Relate to Traditional Usability Indexes?" Proceedings of OZCHI 2005, Canberra, Australia (2005) 10 pp.

Mandryk et al., "A physiological approach for continuously modeling user emotion in interactive play environments" Proceedings of Measuring Behavior (2008) (Maastrichtm the Netherlandsm Aug. 26-29) 2 pp.

Mandryk et al., "Objectively Evaluating Entertainment Technology" Simon Fraser University; CHI (2004) ACM 1-58113-703-6/04/0004; 2 pp.

Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.

Hotz "The Really Smart Phone" The Wall Street Journal, What They Know (2011); 6 pp.; http://online.wsj.com/article/SB10001424052748704547604576263261679848814.html?mod=djemTECH_t.

Evanczuk, S., "PIC MCU software library uses human body for secure communications link" EDN Network; edn.com; Feb. 26, 2013 Retrieved from Internet Jun. 19, 2013 at http://www.edn.com/electronics-products/other/4407842/PIC-MCU-software-library-uses-human-body-for-secure-communications-link; 5 pp.

Gaglani S. "Put Your Phone, or Skin, on Vibrate" MedGadget (2012) http://medgadget.com/2012/03/put-your-phone-or-skin-on-vibrate.html 8pp.

Halthion Medical Technologies "Providing Ambulatory Medical Devices Which Monitor, Measure and Record" webpage. Online website: http://www.halthion.com/; downloaded May 30, 2012.

Jimbo et al., "Gastric-fluid-utilized micro battery for micro medical devices" The Sixth International Workshop on Micro and Nanotechnology for Power Geneartion and Energy Conservation Applications, (2006) pp. 97-100.

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Platt, D., "Modulation and Deviation" AE6EO, Foothills Amateur Radio Society; Oct. 26, 2007; 61 pp.

Winter, J. et al. "The material properties of gelatin gels"; USA Ballistic Research Laboratories, Mar. 1975, p. 1-157.

Kim et al., "A Semi-Interpenetrating Network System for a Polymer Membrane"; Eur. Polym. J. vol. 33 No. 7; pp. 1009-1014 (1997).

* cited by examiner

CONTROLLED ACTIVATION INGESTIBLE IDENTIFIER

CROSS-REFERENCE TO RELATED APPLICATIONS

Pursuant to 35 U.S.C. §119 (e), this application claims priority to the filing date of: U.S. Provisional Patent Application Ser. No. 60/862,925 filed Oct. 25, 2006 the disclosure of which application is herein incorporated by reference.

INTRODUCTION

Prescription medications are effective remedies for many patients when taken properly, e.g., according to instructions. However, studies have shown that, on average, about 50% of patients do not comply with prescribed medication regimens. A low rate of compliance with medication regimens results in a large number of hospitalizations and admissions to nursing homes every year. In the United States alone, it has recently been estimated that the cost to the resulting from patient non-compliance is reaching $100 billion annually.

Consequently, various methods and apparatus have been made available to improve patient compliance with pre- scribed regimens in efforts to improve patient health. To date, many different types of "smart" packaging devices have been developed. In some cases, such devices automatically dis- pense the appropriate pill. In other cases, there are electronic controls that detect and record when the pill is taken out of the box.

While devices and protocols have been developed for improving patient compliance, there is continued interest in the development of new ways of monitoring patient compli- ance. It would be an important advancement in clinical medi- cine if the actual administration and ingestion of a pharma- ceutical, such as a pill being dissolved in the stomach, could be monitored in an automatic and accurate manner without dependence on patient or medical staff reporting, where the signal generated by the identifier in the composition is pro- duced upon contact of the composition with a target location.

One system that meets the above needs is the pharma- informatics system described in PCT application serial no. PCT/US2006/016370 filed on Apr. 28, 2006 and published as WO 2006/116718, the disclosure of which is herein incorpo- rated by reference. While the system described in this appli- cation provides for many benefits, reliability of signal gen- eration can be an issue under certain situations. For example, depending on how the pharmaceutical composition is ingested, the particular contents of the stomach can have a significant impact on how the identifier in the composition activates. For example, signal generation can be affected by the liquid with which a composition is ingested, e.g., water, juice, etc.

As such, of interest would be the development of an improved pharma-informatics system in which the activation of the identifier was highly controlled, such that the signal generated by the identifier would be independent of the par- ticularly environment, e.g., stomach contents, the target site where activation is desired. The present invention provides, for the first time, such a capability.

SUMMARY

The present invention provides for the controlled activation of ingestible identifiers, e.g., as may be incorporated into pharma-informatics enabled pharmaceutical compositions, as may be present in ingestible event markers, etc. Embodi- ments of the controlled activation identifiers of the invention provide for robust and reliable use despite the presence of variable conditions in the applications in which they are employed, e.g., inadequate degradation of a pharmaceutical carrier, variations in the environment of the target site of interest, etc.

The controlled activation identifiers of the invention are identifiers that are activated upon association with a target site of a body. The controlled activation identifier is one that is activated by the presence of a predetermined specific stimulus at the target site, e.g., liquid (wetting), time, pH, ionic strength, conductivity, presence of biological molecules (e.g., specific proteins or enzymes that are present in the stomach, small intestine, colon), blood, temperature, specific auxiliary agents (foods ingredients such as fat, salt, or sugar, or other pharmaceuticals whose co-presence is clinically relevant), bacteria in the stomach, pressure, light, etc. The predeter- mined specific stimulus is a known stimulus for which the controlled activation identifier is designed or configured to respond by activation. In certain embodiments, the signal generated by the identifier is independent of the environment of the target site, e.g., the nature of the fluid at the target site.

The controlled activation identifier includes a controlled activation element that may include one or more components, where the one or more components provide for the desired controlled activation in response to the presence of the pre- determined specific stimulus at the target site. In certain embodiments, the controlled activation identifier includes a dried conductive medium precursor composition (e.g., a dried salt composition) as the controlled activation element, where this element, upon contact with a fluid (such as stomach fluid), produces a conductive medium resulting in activation of the power source and production of an identifying signal. The presence of the dried conductive medium precursor in the power source provides for a number of advantages, including the ability to obtain reliable activation of the identifier despite variations in the environment of the target site (e.g., variations in terms of stomach content composition), where activation of the identifier is desired. In yet other embodiments, the controlled activation identifier includes a barrier as the con- trolled activation element, e.g., in the form of a protective film, that is configured to provide for activation of the iden- tifier upon association with the target site of interest. Other types of controlled activation elements include two or more components, such as a dried conductive medium and a barrier, e.g., as described in more detail below.

The broadcasted signal from the identifier may be received by another device, e.g., a receiver, either inside or near the body, which may then record that the identifier, e.g., one that is associated with one or more active agents and pharmaceu- tical composition, has in fact reached the target site.

DETAILED DESCRIPTION

Figure 1:
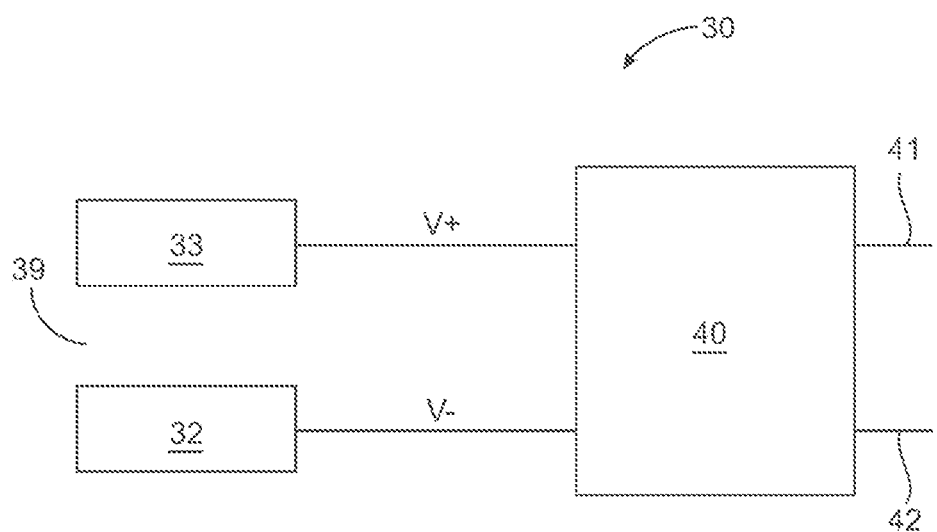
FIG. 1 shows diagrammatically the effects of the pill inges- tion where some of the pill has eroded away.

The controlled activation identifiers of the invention are identifiers that may be activated upon contact with the target site in response to a specific predetermined stimulus. In certain embodiments, controlled activation is provided despite wide variations in the compositional makeup of the target site. As such, the controlled activation identifier provides for reliable and robust data concerning contact of the composition with the target site in the body, where the provided data is substantially, if not completely, independent of any variations in the environment of the target site. Accordingly, despite wide variations in the composition make up of the target site, e.g., stomach, that may be encountered in using the subject identifiers, the identifiers provide for consistent and reliable signals that are not affected by the composition of the target site environment. The applications of this new information device and system are multi-fold and described in further detail in PCT application Serial No. US2006/016370 titled "Pharma-Informatics System," and published as WO 2006/116718, and U.S. Provisional application Ser. No. 60/949,223 and titled "Ingestible Event Marker"; the disclosure of which applications described therein are incorporated by reference, as well as in the applications reviewed below.

In further describing the invention in greater detail, embodiments of the compositions are reviewed first, followed by a discussion of systems including the subject compositions, methods of using the subject compositions and systems and various illustrative applications in which the compositions and methods find use. Also reviewed in greater detail below are kits that include the subject compositions.

Compositions

Embodiments of the invention include a controlled activation identifier, where the identifier may be associated with a carrier composition, e.g., a pharmaceutically acceptable vehicle, and may or may not be associated with one or more pharmaceutical active agents. In certain embodiments, the compositions are disrupted upon administration to a subject. As such, in certain embodiments, the compositions are physically broken, e.g., dissolved, degraded, eroded, etc., following delivery to a body, e.g., via ingestion, etc. The compositions of these embodiments are distinguished from devices that are configured to be ingested and survive transit through the gastrointestinal tract substantially, if not completely, intact.

As summarized above, the compositions include a controlled activation identifier and an active agent/carrier component. Each of these different components are reviewed separately in greater detail below.

Controlled Activation Identifiers

As summarized above, the compositions of the invention include controlled activation identifiers. The controlled activation identifiers of the present compositions may vary depending on the particular embodiment and intended application of the composition so long as they are activated (i.e., turned on) upon association with or contact with a target physiological location, e.g., stomach, small intestine, large intestine, etc. In certain embodiments, activation occurs in a manner that is substantially, if not completely, environment independent, but for the presence of the predetermined activating stimulus (e.g., fluid, chemical agent, light) that is present at the target site of interest. As such, the identifier may be an identifier that emits a signal when it contacts a target body (i.e., physiological) site, where the nature of the signal is not substantially affected, if affected at all, by the particular makeup of the environment of the target site, apart from the presence of the actual activating stimulus. For example, if the target site is the stomach, the activation of the identifier will be substantially if not completely the same under a variety of different stomach content conditions, e.g., pH variations ranging from about 1 to about 8, etc., where apart from the presence of the fluid stimulus (the activator being activated by wetting) the pH of the fluid does not impact how the identifier is activated. As such, the identifiers are, in certain embodiments, characterized by emitting the same signal in terms of timing and strength following contact with a variety of different fluid compositions having a variety of different pH values. In addition or alternatively, the identifier may be an identifier that emits a signal when interrogated after it has been activated, where activation still occurs in a controlled manner that is independent of target site environment, as reviewed above.

Depending on the needs of a particular application, the signal obtained from the identifier may be a generic signal, e.g., a signal that merely identifies that the composition has contacted the target site, or a unique signal, e.g., a signal which in some way uniquely identifies that a particular composition from a group or plurality of different compositions in a batch has contacted a target physiological site. As such, the identifier may be one that, when employed in a batch of unit dosages, e.g., a batch of tablets, emits a signal which cannot be distinguished from the signal emitted by the identifier of any other unit dosage member of the batch. In yet other embodiments, the identifier emits a signal that uniquely identifies a given unit dosage, even from other identical unit dosages in a given batch. Accordingly, in certain embodiments the identifier emits a unique signal that distinguishes a given type of unit dosage from other types of unit dosages, e.g., a given medication from other types of medications. In certain embodiments, the identifier emits a unique signal that distinguishes a given unit dosage from other unit dosages of a defined population of unit dosages, e.g., a prescription, a batch or a lifetime production run of dosage formulations. In certain embodiments, the identifier emits a signal that is unique, i.e., distinguishable, from a signal emitted by any other dosage formulation ever produced, where such a signal may be viewed as a universally unique signal (e.g., analogous to a human fingerprint which is distinct from any other fingerprint of any other individual and therefore uniquely identifies an individual on a universal level). In one embodiment, the signal may either directly convey information about the composition, or provide an identifying code, which may be used to retrieve information about the composition from a database, i.e., a database linking identifying codes with compositions.

The identifier may be any component or device that is capable of providing a detectable signal following controlled activation, e.g., upon contact with the target site. In certain embodiments, the identifier emits a signal once the composition comes into contact with a physiological target site, e.g., as summarized above. For example, a patient may ingest a pill that, upon contact with the stomach fluids, generates a detectable signal.

Depending on the embodiment, the target physiological site or location may vary, where representative target physiological sites of interest include, but are not limited to: a location in the gastrointestinal tract (such as the mouth, esophagus, stomach, small intestine, large intestine, etc.); another location inside the body, such as a parental location, vascular location, etc.; or a topical location; etc. In certain embodiments, the identifier is configured to be activated upon contact with fluid in the target site, regardless of the particular composition of the target site.

In certain embodiments, the identifier is dimensioned to be orally ingestible, e.g., either by itself or upon combination with a physiologically acceptable carrier component of the composition so as to produce a composition that can be readily administered to a subject in need thereof. As such, in certain embodiments, the identifier element is dimensioned to have a width ranging from about 0.05 to about 2 or more mm, e.g., from about 0.05 mm to about 1 mm, such as from about 0.1 mm to about 0.2 mm; a length ranging from about 0.05 to about 2 or more mm, e.g., from about 0.05 mm to about 1 mm, such as from about 0.1 mm to about 0.2 mm and a height ranging from about 0.05 to about 2 or more mm, e.g., from about 0.1 mm to about 1 mm, such as from about 0.05 mm to about 0.3 mm, including from about 0.1 mm to about 0.2 mm. In certain embodiments the identifier is 1 $mm^3$ or smaller, such as 0.1 $mm^3$ or smaller, including 0.2 $mm^3$ or smaller. The identifier element may take a variety of different configurations, such as but not limited to: a chip configuration, a cylinder configuration, a spherical configuration, a disc configuration, etc, where a particular configuration may be selected based on intended application, method of manufacture, etc.

The identifier may generate a variety of different types of signals, including but not limited to: RF signals, magnetic signals, conductive (near field) signals, acoustic signals, etc. Of interest in certain embodiments are the specific signals described in PCT application serial no. PCT/US2006/16370 titled "Pharma-Informatics System" and filed on Apr. 28, 2006 and published as WO 2006/116718; the disclosures of various types of signals in these applications being specifically incorporated herein by reference.

The transmission time of the identifier may vary, where in certain embodiments the transmission time may range from about 0.1 μsec to about 48 hours or longer, e.g., from about 0.1 μsec to about 24 hours or longer, such as from about 0.1 μsec to about 4 hours or longer, such as from about 1 sec to about 4 hours. Depending on the given embodiment, the identifier may transmit a signal once or transmit a signal two or more times, such that the signal may be viewed as a redundant signal.

In certain embodiments, the identifier may be one that is programmable following manufacture, in the sense that the signal generated by the identifier may be determined after the identifier is produced, where the identifier may be field programmable, mass programmable, fuse programmable, and even reprogrammable. Such embodiments are of interest where uncoded identifiers are first produced and following incorporation into a composition are then coded to emit an identifying signal for that composition. Any convenient programming technology may be employed. In certain embodiments, the programming technology employed is RFID technology. RFID smart tag technology of interest that may be employed in the subject identifiers includes, but is not limited to: that described in U.S. Pat. Nos. 7,035,877; 7,035,818; 7,032,822; 7,031,946, as well as published application no. 20050131281, and the like, the disclosures of which are herein incorporated by reference. With RFID or other smart tag technology, a manufacturer/vendor may associate a unique ID code with a given identifier, even after the identifier has been incorporated into the composition. In certain embodiments, each individual or entity involved in the handling of the composition prior to use may introduce information into the identifier, e.g., in the form of programming with respect to the signal emitted by the identifier, e.g., as described in U.S. Pat. No. 7,031,946 the disclosure of which is herein incorporated by reference.

The identifier of certain embodiments includes a memory element, where the memory element may vary with respect to its capacity. In certain embodiments, the memory element has a capacity ranging from about 1 bit to 1 gigabyte or more, such as 1 bit to 1 megabyte, including from about 1 bit to about 128 bit. The particular capacity employed may vary depending on the application, e.g., whether the signal is a generic signal or coded signal, and where the signal may or may not be annotated with some additional information, e.g., name of active agent, etc.

Controlled activation identifier components of embodiments of the invention have: (a) a controlled activation element made up of one or more components; and (b) a signal generation component, where the signal generation component is activated by the controlled activation component to produce an identifying signal, e.g., as described above.

Controlled Activation Component

The controlled activation component is a component that activates the signal generation element of the identifier to provide a signal, e.g., by emission or upon interrogation, following contact of the composition with a target physiological site of interest, such as the stomach. The controlled activation component is configured to be activated in a manner that is substantially, if not completely, independent of the particularly compositional makeup of the target site, such that activation is independent of the compositional makeup of the target site.

As reviewed in PCT application serial no. PCT/US2006/16370 titled "Pharma-Informatics System" and filed on Apr. 28, 2006 and published as WO 2006/116718, activation of the identifier may be achieved in a number of different ways, where such approaches include, but are not limited to: battery completion, battery connection, etc. The different activation approaches disclosed in this copending application may be readily adapted to provide controlled activation, as described herein, and as such are herein incorporated by reference in their entirety.

For example, controlled activation elements based on battery completion formats may employ a battery that includes, when completed, a cathode, an anode, and an electrolyte. When the composition is administered, e.g., ingested, and travels through the esophagus, it proceeds to enter the stomach. The cathode and anode provided within the composition do not constitute a full battery. However, as the composition dissolves to expose the cathode and anode, the stomach fluid (either by itself or when combined with a dried conductive precursor medium component of the identifier) acts as the electrolyte component of the battery. The added component of the stomach fluid thus completes the battery. Therefore, as the composition contacts the target site, e.g., by entering the stomach and dissolving to the point of cathode and anode exposure, a power source is provided which activates the identifier, e.g., in chip configuration. The data signal is then transmitted.

In certain embodiments, the battery that is employed is one that comprises two dissimilar electrochemical materials which constitute the two electrodes (e.g., anode and cathode) of the battery. When the electrode materials are exposed and come in contact with the body fluid, such as stomach acid or other types of fluid (either alone or in combination with a dried conductive medium precursor, as reviewed below), a potential difference, that is, a voltage, is generated between the electrodes as a result of the respective oxidation and reduction reactions incurred to the two electrode materials. A voltaic cell, or battery, can thereby be produced. Accordingly, in embodiments of the invention, such batteries are configured such that when the two dissimilar materials are exposed to the target site, e.g., the stomach, the digestive tract, etc., during the physical and chemical erosion of the composition in which the signal generation element is present, a voltage is generated. The two dissimilar materials in an electrolyte are at different potentials, similar to the physics model of a 'potato battery'. As an example, copper and zinc when put into a cell have different potentials. Similarly, gold and magnesium have different potentials. As a result, a potential difference between the two dissimilar materials is generated.

In certain of these embodiments, the battery power source may be viewed as a power source that exploits electrochemical reaction in an ionic solution such as gastric fluid, blood, or other bodily fluids and some tissues. FIG. 1 provides a diagrammatic representation of the events which occur when the pill is ingested and dissolved to the point that some of the pill has been chemically and/or physically eroded away. Electrode materials 32 and 33 are now in an ionic solution 39 (which may be made up of target site fluid alone or target site fluid combined with a dried conductive medium precursor). This configuration creates a low voltage (V−) and a high voltage (V+) as applied to an electronic circuit 40. The two outputs of that electronic circuit 40 are E0 41 and E1 42, which are the signal-transmission electrodes on the top surface. In an alternate embodiment no shown in FIG. 2 where the signal generation element 30 includes a single electrode, the output is E0 41.

Figure 2:
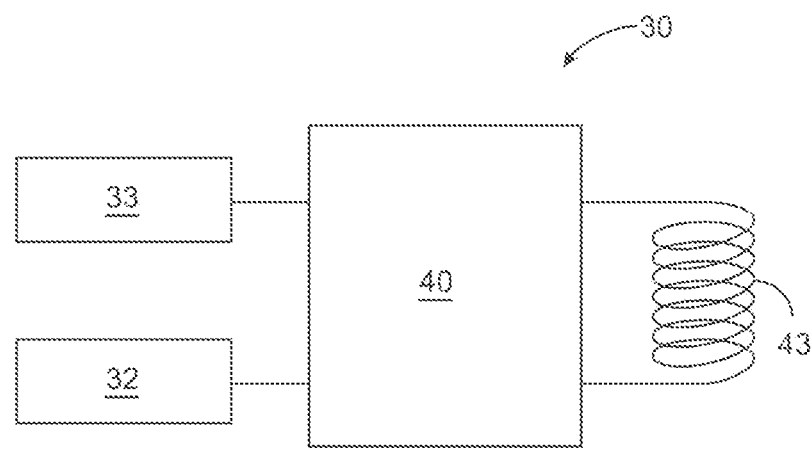
FIG. 2 provides a similar arrangement to FIG. 1, with a coil rather than two electrodes as the output.

FIG. 2 shows a similar arrangement as in FIG. 1. However, instead of having two electrodes as the output, a coil is provided. Electrode materials 32 and 33 are applied to the electronic circuit 40 of signal generation element 30. The outputs of the electronic circuit 40 are coupled to a coil 43. This configuration provides that a battery is created by Electrode materials 32 and 33 when exposed to ionic solution. This battery drives the circuit 40, which creates an oscillating frequency. This oscillating current goes through the coil and generates a RF magnetic signal. Unlike near-field quasi-static electrical signals, which may suffer from significant attenuation through body tissues, the RF magnetic signal can be transmitted through body tissues with less attenuation. The RF magnetic signal is then picked up by an external or internal receiver device that has a magnetic-signal detection mechanism. If a broadcast is provided at a high enough frequency, a pager-like device that is worn by the patient will detect whenever a pill is ingested.

FIGS. 1 and 2 illustrate an identifier 30 having a signal generation element 40 powered by electrochemical reaction. Signal generation element 40 is electrically connected to electrode electrodes 32 and 33, which are made of two different materials and are electrically insulated from each other. When electrodes 32 and 33 are immersed in an ionic solution 39, a potential difference develops between them; for instance, electrode 33 rises to a higher potential V+ while electrode 32 falls to a lower potential V−. This potential difference can be used to power circuitry 40.

Electrodes 32 and 33 can be implemented in various ways; for instance, areas on opposing surfaces of an integrated circuit chip can be coated with two different metals, and the entire chip can be placed in the ionic solution. Alternatively, electrodes 32 and 33 may extend away from element 40 as shown. Other arrangements may also be used.

Electrodes 32 and 33 can be made of any two materials appropriate to the environment in which the identifier 30 will be operating. The active materials are any pair of materials with different electrochemical potentials. For instance, in some embodiments where ionic solution 39 comprises stomach acids, electrodes 32 and 33 may be made of a noble metal (e.g., gold, silver, platinum, palladium or the like) so that they do not corrode prematurely. Alternatively, the electrodes can be fabricated of aluminum or any other conductive material whose survival time in the applicable ionic solution is long enough to allow identifier 30 to perform its intended function. Suitable materials are not restricted to metals, and in certain embodiments the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

A variety of different materials may be employed as the battery electrodes. In certain embodiments, electrode materials are chosen to provide for a voltage upon contact with the target physiological site, e.g., the stomach, sufficient to drive the signal generation element of the identifier. In certain embodiments, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain embodiments, the voltage ranges from about 0.001 to about 10 volts, such as from about 0.01 to about 10 V.

Materials and pairings of interest include, but are not limited to those reported in Table 1 below.

TABLE 1

|  | Anode | Cathode |
| --- | --- | --- |
| Metals | Magnesium, Zinc Sodium (†), Lithium (†) Iron and alloys thereof | |
| Salts | | Copper salts: iodide, chloride, bromide, sulfate, formate, (other anions possible) $Fe^{3+}$ salts: e.g. orthophosphate, pyrophosphate, (other anions possible) Oxygen (††) on platinum, gold or other catalytic surfaces |
| Intercalation compounds | Graphite with Li, K, Ca, Na, Mg | Vanadium oxide Manganese oxide |

(†) Protected anodes: certain high energy anode material such as Li, Na, and other alkali metals are unstable in their pure form in the presence of water or oxygen. These may however be used in an aqueous environment if stabilized. One example of this stabilization is the so-called "protected lithium anode" developed by Polyplus Corporation (Berkeley, CA), where a polymer film is deposited on the surface of lithium metal to protect it from rapid oxidation and allow its use in aqueous environment or air ambient. (Polyplus has IP pending on this).
(††) Dissolved oxygen can also serve as a cathode. In this case, the dissolved oxygen in the bodily fluids would be reduced to OH— at a suitable catalytic surface such at Pt or gold. Other catalysts are also possible.

In certain embodiments, one or both of the metals may be doped with a non-metal, e.g., to enhance the voltage output of the battery. Non-metals that may be used as doping agents in certain embodiments include, but are not limited to: sulfur, iodine and the like.

In certain embodiments, the electrode materials are cuprous iodine (CuI) or cuprous chloride as the anode and magnesium (Mg) metal or magnesium alloy as the cathode. Embodiments of the present invention use electrode materials that are not harmful to the human body.

Additional battery configurations of interest include, but are not limited to, those described in: U.S. Provisional Application Ser. No. 60/889,868 titled "Pharma Informatics System Power Source," and filed on Feb. 14, 2007; U.S. Provisional Application Ser. No. 60/889,870 titled "Pharma Informatics System Power Source Having High Surface Area Cathodes," and filed on Feb. 14, 2007; and U.S. Provisional Application Ser. No. 60/889,871 titled "Pharma Informatics System Having Short Resistant Series Battery"; the disclosures of which applications are herein incorporated by reference.

The controlled activation element of the identifier that provides for controlled activation may be responsive to a variety of different types of stimuli. Stimuli of interest for which the controlled activation element can be configured to be responsive to include but are not limited to: liquid (wetting), time, pH, ionic strength, conductivity, biological molecules (e.g. specific proteins or enzymes that are present in the stomach, small intestine, colon), blood, temperature, specific auxiliary agents (foods ingredients such as fat, salt, or sugar, or other pharmaceuticals whose co-presence is clinically relevant), bacteria in the stomach, pressure, and light.

The controlled activation element is made up of one or more components that provides for the desired controlled activation functionality, such that the controlled activation element is responsive to the stimulus of interest. The nature of the component or components that make up the controlled activation element may vary. For example, where the stimulus of interest is temperature, the controlled activation element may be a barrier of a material, such as a film (e.g., a polymeric film) whose solubility is a function of temperature, specifically one that becomes soluble at or near body temperature. Such a film may be insoluble/impermeable to water at room temperature but soluble/permeable at 37° C. Materials of interest that may be used for such films include, but are not limited to the polymeric materials listed below. In those embodiments where pressure is the stimuli of interest, the controlled activation element may be a pressure sensitive material, e.g., a capsule or shell (for example, made of a cellulosic material), that has a specific mechanical strength such that at a pressure threshold above the threshold the element will be crushed and allow the identifier to be activated and transmit a signal. In other embodiments of interest, the stimulus may be light. For example, the stimulus may be a fluorescent label which has been attached to a tumor. As the identifier passes by the tumor, the controlled activation element may include a component that provides light at a stimulating wavelength for the label and also a component that detects emitted light from the label. Any convenient light source and detector may be employed. When the detector component detects the emitted light, it will activate the identifier in a controlled activation manner.

Figure 3:
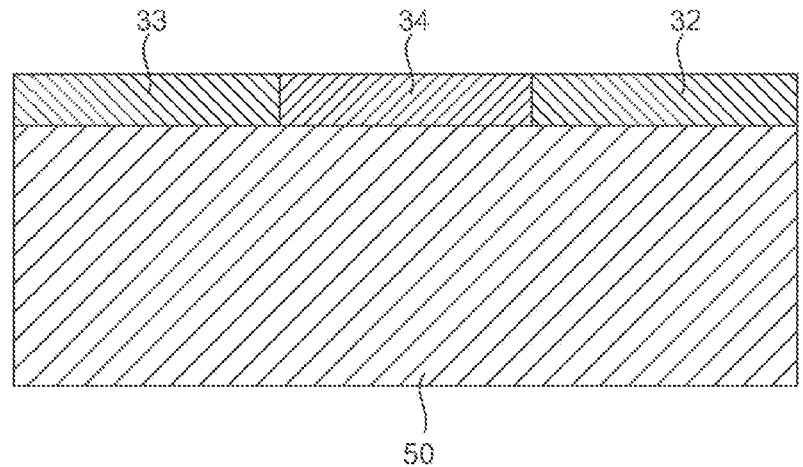
FIGS. 3 to 8 provide different views of controlled activa- tion batteries in accordance with different embodiments of the invention.

In certain embodiments, the one or more controlled activation components of the invention provide for controlled activation, i.e., activation in a manner that is substantially, if not completely, independent of target site environment, as reviewed above. In one embodiment of interest, the controlled activation component includes a dried conductive medium that, upon combination with target site fluid, produces an ionic medium in the presence of the first and second dissimilar materials to activate the battery, e.g., as reviewed above. A representative configuration of such activation component that includes a dried conductive medium precursor component is provided in FIG. 3. FIG. 3 shows battery element with electrode materials 32 and 33 present on a surface of solid support 50. Positioned between electrode materials 32 and 33 is dried conductive medium precursor 34.

When present, the dried conductive medium precursor may be any of a variety of different types of compositions. Compositions of interest include, but are not limited to: salts of physiologically acceptable electrolytes, such as but not limited to: sodium ion, chloride ion, potassium ion and calcium ion, magnesium ion, etc. Specific physiologically compatible salts of interest include, but are not limited to: KCl, NaCl, $MgCl_2$, and the like. Aspects of the invention include the presence of a dried conductive medium precursor. When the precursor is a salt, e.g., as described above, the dried salt may be provided in any convenient format, such as a lyophilized salt composition.

Figure 4:
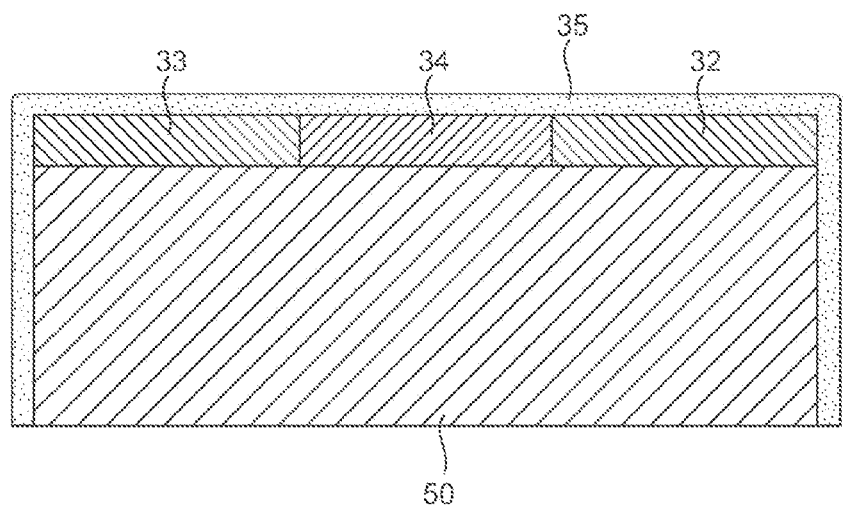

A variation of the embodiment shown in FIG. 3 is depicted in FIG. 4. In FIG. 4, the identifier includes a protective barrier, where the protective barrier serves to retain dried conductive medium precursor. The protective barrier 35 may have a variety of different configurations and functions, in addition to serving to retain the precursor with the identifier. For example, the protective barrier 35 may serve to provide for controlled metering of target site liquid to the dried conductive medium precursor 34. In FIG. 4, ion permeable membrane 35 is provided which controls which portion of the target site fluid combines with the dried conductive medium precursor 34 to activate the battery. Any convenient semi-permeable membrane may be employed. The semi-permeable membrane may comprise ePTFE, Dacron®, polyurethane, silicone rubber, poly(lactide-co-glycolide) (PLGA), poly(caprolactone) (PCL), poly(ethylene glycol) (PEG), collagen, polypropylene, cellulose acetate, poly(vinylidene fluoride) (PVDF), nafion or other biocompatible material. The pore size of the membrane may vary depending on the particular configuration, where in certain embodiments the membrane have a pore size (MW cutoff of about 1000 d or less, such as about 500 d or less, including about 250 d or less, e.g., about 100 d or less, such as about 50 d or less). In certain embodiments, the membrane is a water only permeable membrane, such that water, but little if any other fluid constituents at the target site, pass through the membrane to reach to the dried conductive medium precursor of the identifier.

Figure 5:
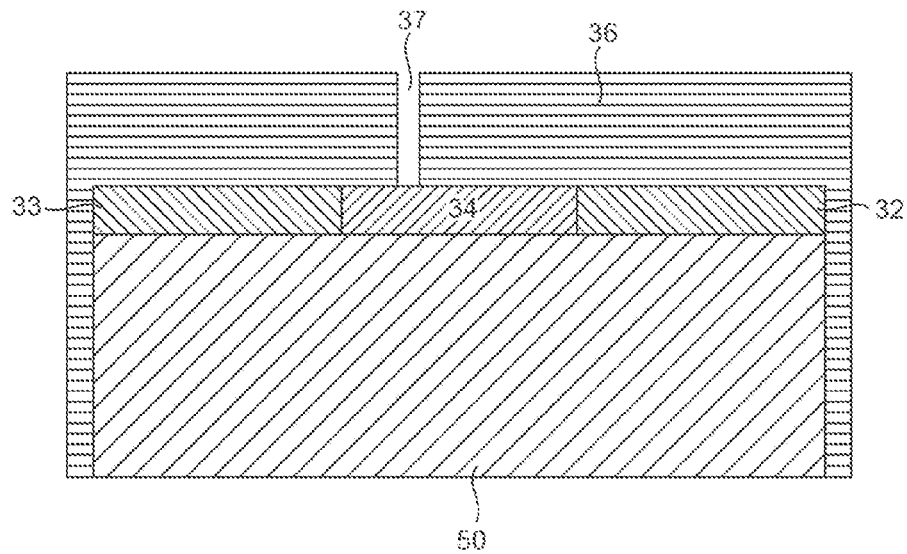

Instead of a semi-permeable membrane, a solid barrier that includes one or more fluid flow paths may be present. For example, in FIG. 5, the battery includes solid barrier 36 which includes a fluid flow path 37. While fluid flow path 37 may have any convenient dimensions, in certain embodiments fluid flow path is a capillary flow path, such that fluid flows through the flow path via capillary action. In certain embodiments, the fluid flow path has microscale cross-sectional inner dimensions such that the independent dimensions are greater than about 1 µm and less than about 1000 µm. These independent cross sectional dimensions, i.e. width, depth or diameter depending on the particular nature of the fluid flow path or channel, may range from about 1 to 200 µm, such as from about 10 to 150 µm, and including from about 20 to 100 µm with, the total inner cross sectional area ranging from about 100 to 40,000 µm², such as from about 200 to 25,000 µm². The inner cross sectional shape of the channel may vary greatly. Configurations include, but are not limited to: rectangular, square, rhombic, triangular or V-shaped, D-shaped, U-shaped, circular, semicircular, ellipsoid and the like. While the fluid flow path as shown in FIG. 5 is straight, the flow path may, course, have a variety of different configurations, such that it may include bends or turns, be curvilinear, etc., as desired. Any convenient fabrication techniques may be employed, where "lab on-a-chip" technologies, such as but not limited to those described in U.S. Pat. Nos. 6,939,451; 6,838,156; 6,730,206; 6,623,860; 6,613,525; 6,306,273; 6,284,113; 6,176,962; 6,103,199; 6,056,860; 6,054,034;

5,935,401; 5,858,188; 7,069,952; 7,033,474; 6,857,449; 6,841,193; 6,660,367; 6,551,836; 6,517,234; 6,509,085; the disclosures of which are herein incorporated by reference.

In certain embodiments, the surface of the flow path may be modified to provide for desired fluid flow properties. For example, the surface energy of one or more surfaces of the flow path may be modified to provide for enhanced fluid flow through the capillary. For example, the surface energy of one or more surfaces of the flow path may be increased, such that the surface becomes more hydrophilic. A variety of different surface energy modification protocols may be employed, where the particular protocol chosen may depend on the particular composition of the barrier and the desired surface energy properties. For example, if one wishes to increase the surface energy of a given surface, the surface may be subjected to plasma treatment, contacted with a surface energy modification such as surface modifying polymer solutions described in, e.g., U.S. Pat. Nos. 5,948,227 and 6,042,710, each of which is incorporated herein in its entirety for all purposes.

In certain embodiments, the barrier may be one that disrupts upon contact with a fluid having sufficient conductivity to activate the identifier in a predetermined manner, either alone or in combination with dried conductive medium precursor that may be present on the support. For example, FIG. 6 shows an embodiment where a barrier 38 is present that, upon contact with a fluid meeting predetermined criteria, e.g., conductivity, pH, etc., disrupts (such as by dissolution) to expose dried conductive medium precursor 34 to fluid and thereby activate the battery.

Figure 6:
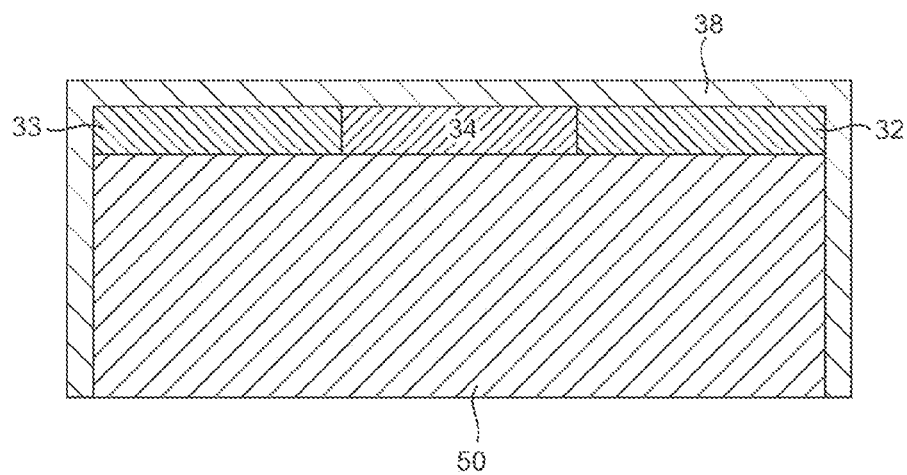
Figure 7:
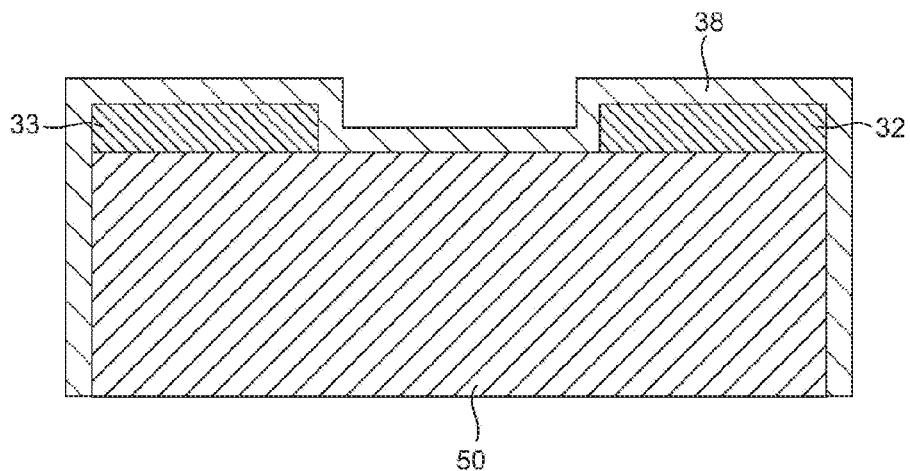

While FIG. 6 shows the presence of such a barrier with a dried precursor, the dried precursor need not be present. For example, FIG. 7 shows an embodiment where a dried conductive medium precursor is not present. In this embodiment, protective layer 38 protects electrodes 32 and 33 and substrate 50. Upon contact with a fluid meeting predetermined criteria, e.g., conductivity, pH, etc., protective layer 38 disrupts (such as by dissolution) to expose dried electrodes 32 and 33 to fluid and thereby activate the battery.

Figure 8:
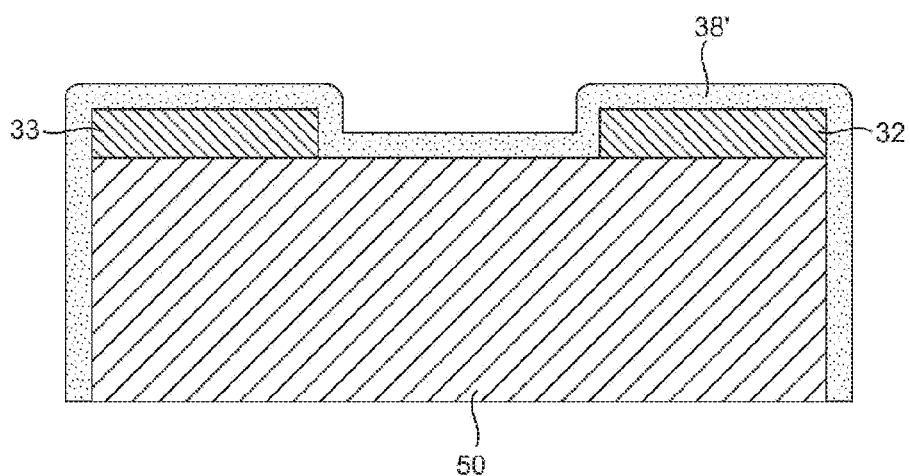

A variation of the embodiment shown in FIG. 7 is provided in FIG. 8. In FIG. 8 barrier 38' is a time controlled dissolution composition, i.e., a composition that dissolves in a time dependent manner upon contact with a fluid, where the dissolution time of a given material in the fluid of interest is known prior to contact with the fluid, such that the dissolution time is predetermined. In certain embodiments, this composition is a polymer composition, such as a polymer composition employed in time controlled release pharmaceutical compositions. Polymeric compositions of interest that may be employed include, but are not limited to: water-swellable compositions (whose thickness imparts controlled time dissolution), such as compositions made up of a binder (such as vinyl polymers, such as polyvinylpyrrolidone, polyvinyl alcohol, and the like; cellulosic polymers, such as hydroxypropylmethylcellulose, hydroxyethylcellulose, hydroxypropylcellulose, and the like; acrylic polymers and copolymers such as methacrylic acid copolymers, ethyl acrylate-methylmethacrylate copolymers, and the like; natural or synthetic gums, such as guar gum, arabic gum, xanthan gum, and the like; proteins or carbohydrates, such as gelatin, pectin, and the like; and mixtures thereof) and a polymeric coating particle (such as particles made up of cellulosic polymers, such as methylcellulose, carboxymethylcellulose, hydroxypropylcellulose, hydroxypropylmethylcellulose, hydroxyethylcellulose, and the like; vinyl polymers, such as polyvinylpyrrolidone, polyvinyl alcohol, and the like; acrylic polymers and copolymers, such as acrylic acid polymer, methacrylic acid copolymers, ethyl acrylate-methyl methacrylate copolymers, and the like; and mixtures thereof) and described in U.S. Pat. No. 6,190,692 (the disclosure of which is herein incorporated by reference); and the like.

It is noted that with the time-delay configuration as exemplified by the embodiment of FIG. 8, it is not necessary for the barrier, e.g., membrane, to cover both electrodes and the space in between. In certain embodiments, only one electrode is covered and subsequently activated, since the battery will not discharge unless both electrodes are activated. As such, in certain embodiments just one electrode covered by a "patch" of material that dissolves away, resulting in activation.

The above discussion, in combination with FIGS. 1 to 8, provides details of certain non-limiting embodiments of the controlled activation elements of the subject identifiers. As described above, the controlled activation element may include a single component, e.g., a barrier, a dried conductive medium, etc., or be a composite controlled activation element of two or more components that work together to provide controlled activation functionality to the identifier (e.g., where the controlled activation element includes both a barrier and a dried conductive medium. In certain embodiments, the various controlled activation mechanisms described above can be combined to achieve cascaded or multi-component activation. For example, several types of film can be deposited or otherwise present on an identifier, or a film-based activation can be combined with a capsule-based activation and a salt-based activation. Examples of such schemes include but are not limited to the following.

In one embodiment, several layers of film are present on the identifier, so that the first layer protects the identifier during processing/storage, the second layer dissolves when a target pH is reached, and the third layer releases a salt to finally activate the device and transmit a signal. Advantages of this type of approach include additional protection and margin against accidental or premature activation. The device can only activate once all the activation events have occurred. Another use of a multilayered film is as an anti-tempering mechanism, because the identifier will activate only after the specific sequence of conditions have been encountered, which makes it difficult or impossible to incorrectly active the device by dipping it into a single fluid or holding it in the mouth without swallowing.

Another example is multiple patches of activating films that are deposited on different parts of the activating surface of the identifier, e.g., the electrodes. For example, the battery on the identifier may be micropatterned or covered by several micropatterned patches of film that activate in different parts of the GI tract, so that a signal is transmitted by an identifier once it reaches the stomach, then transmitted again when the identifier reaches the intestine, and again when it reaches the colon, etc. This configuration allows the same identifier to detect multiple events, such as passage through different parts of the GI tract.

Another use of combined activation is for the identifier to detect a combined event, e.g., to detect when a patient has ingested an identifier along with a certain type of food, drink, or other medication. This allows detection of interactions or of patients ingesting things they are not supposed to with their medication.

Another use in certain embodiments is to transmit a different signal depending on different conditions in the GI tract. An identifier may be built with two separate transmitting elements that are activated via different mechanisms, so that in addition to activation of the identifier information can be obtained about the GI tract's condition. For example, one element is activated by a low pH condition and the other, in a high pH condition.

Figure 12:
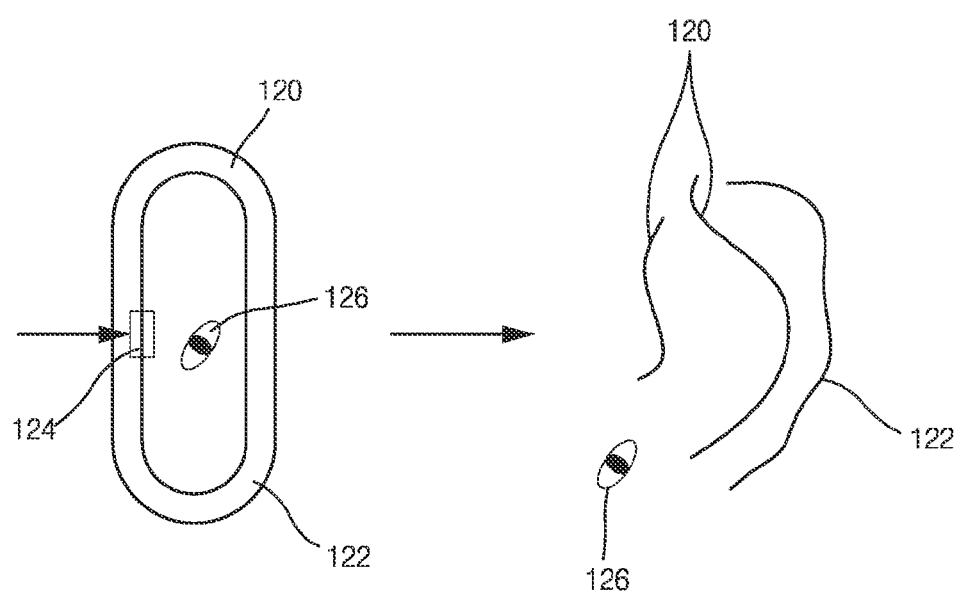
FIG. 12 provides a schematic of an identifier encased in a disruptable controlled activation element according to an embodiment of the invention.

Identifiers of the invention may be associated with carrier compositions that can potentially interfere with the functionality of the identifier if the carrier does not degrade properly upon ingestion. For example, a typical gel capsule (e.g., made by Capsugel, Peapack, N.J.) dissolves in aqueous solutions in a manner that is strongly dependent on physical (e.g., temperature) and chemical environment of the device. Under certain combinations of conditions, the gel residue may only dissolve partially, leaving an undissolved or congealed layer or residue on the surface of an identifier associated with the capsule. Such remaining residue can completely prevent activation of the device or reduce signal strength. Where the identifier is configured to be associated with a gel capsule formulation or analogous carrier structure, in certain embodiments the controlled activation element is one which is designed to ensure that when the intended activation time or chemical/physical environment is reached, the device is not hindered by residue from a carrier such as a gel capsule. One configuration designed to present remaining residue from interfering with function of the device includes a soluble film deposited on the device surface such that the partially dissolved gel residue adheres to this film. Upon ingestion, the film then dissolves away in a timed or chemically-sensitive manner, leaving the device surface free of gel. In another approach, an absorbent substance (e.g. powder or granular form) is added to the gel capsule such that the partially dissolved gel residue adheres to the powder or granules. The powder then falls away from the device. Examples may include any edible powder or granules, such as starch, sugar, salt, or proteins. In another configuration, a substance added to the gel capsule that swells significantly upon wetting, resulting in the bursting of the gel capsules and release of the device. Examples include swelling polymer matrices such as pharmaceutical excipients that are disintegrating agents (the so-called superdisintengrants) and dissolution aids. Examples are Ac-Di-Sol (made by FMC) and carboxymethyl cellulose and related compounds. In yet another embodiments, a substance is added to the gel capsule that generates heat upon dissolution. Gel capsule dissolution is very sensitive to heat. Certain salts undergo exothermic dissolution reaction in water. Such salts can be added to the capsule or deposited on the surface of the device so that upon wetting, sufficient heat is generated to raise the local temperature by a few ° C. (e.g., 0.1 to 20° C., such as 1 to 10° C., including 1 to 5° C.). Examples of these salts are: $ZnC_2$, $BaCl_2$, $MgCl_2$. In yet another embodiment (e.g., as shown in FIG. 12), a strip or sheet 120 of polymeric material (e.g., ethyl cellulose) with a spring-like property is included inside the gel capsule 122. The strip is folded or coiled and constrained at its ends by a water soluble polymer (e.g., hydroxypropyl cellulose) 124. Present inside of the strip is identifier 126. Upon wetting (indicated by arrow), the water soluble polymer 124 dissolves away, allowing the strip 120 or sheet to unfold with enough mechanical force to burst open the gel capsule 122 and release the device 126 clear of the capsule.

In controlled activation elements that include a film or layer, e.g., as described above, the film or layer can be on only one surface of the device or a portion thereof (e.g., it may cover only an active surface of the device or electrode elements present thereon) or it may cover all surfaces of the device, such that the device is encased or encapsulated in the film or layer. In certain embodiments, the identifier device is encapsulated entirely in a polymeric pellet that dissolves in response to chemical/physical environment and/or time. The resultant pellet is placed inside a gel cap or compressed into a tablet, where it also protects the identifier from damage caused by the large compression forces used to make a tablet.

Film barriers have been described in the above discussion in terms of their functionality in providing controlled activation for the identifier. In addition or alternatively to this function, a film barrier may be present that is configured to prevent mechanical damage to the identifier (e.g., damage to IC or battery layers) during processing, handling, bottling, or storage. For example, the device includes in certain embodiments a film that prevents activation or degradation of the device performance or lifetime during processing steps (e.g., when the battery may get wet) or storage (e.g., via moisture absorption from the atmosphere). For example, a film that is soluble only in low pH solution is employed in certain instances to protect the device during processing in high pH aqueous environments. In certain embodiments, a film is present that prevents device-to-device contact (e.g., when multiple devices are placed in the same gel capsule or in a bottle).

Another type of controlled activation identifier is one that is configured so that it is activated only upon elimination of the identifier from the body. For example, the identifier may be covered (partially or wholly) in a barrier layer that is impervious and remains intact while the identifier passes through the GI tract. Upon elimination of the identifier from the GI tract, the barrier may dissolve when it comes in contact with water present in a waste elimination device, e.g., toilet. For example, the barrier may be sensitive to chemicals present in the water of the toilet. When the barrier is disrupted, the water activates the identifier to emit a signal, where the signal may be picked up by a sensor, e.g., associated with the toilet. To prevent tampering, a second controlled activation element that is disrupted by the GI tract may be included, such that activation only occurs when this second element is disrupted by the GI tract and the first barrier is disrupted by the toilet water.

The identifiers may be fabricated using any convenient processing technology, for example, planar processing technology, e.g., as employed in MEMS fabrication, may be employed, coupled with deposition technologies, such as precipitation, for providing the dried conductive medium precursor.

The subject controlled activation batteries may be fabricated in a number of different ways. In certain embodiments, fabrication protocols which may be categorized as "planar" processing protocols are employed, as developed in greater detail below.

After the battery is activated, further activation configurations can be employed to activate the signal generation component. For example, the signal generation component can be activated through the activation of the gate of a metal oxide semiconductor (MOS) circuit, such as a CMOS switch. Activation of the gate of the MOS circuit can be based on one or more parameters, which include but are not limited to: gate current, gate charge, and gate capacitance. The gate current, for activation purposes, can be a function of the conductivity of surrounding body fluids or tissues. Such conductivity can further be a function of one or more parameters, which include but are not limited to: solution concentration, solution pH value, ionic content of solution, enzymatic content of solution, temperature, and carrier mobility. Carrier mobility can also be a function of temperature. Similarly, the gate charge can be a function of one or more parameters, which include but are not limited to: solution composition, crystal potential, electrical potential, gravitational potential, gate capacitance, and carrier concentration. The carrier concentration can also be a function of temperature. The gate capacitance can be a function of the capacitive geometry of the gate, which can further be a function of pressure, a resonant input, or the characteristics of a dielectric material coupled to the gate. The characteristics of the dielectric material can vary with one or more parameters, which include but are not limited to: chemical contents of a digestive tract, chemical character of a physiological location, and amount of dissolution of the dielectric material in body fluids.

Signal Generation Component

The signal generation component of the identifier element is a structure that, upon activation by the controlled activation component, emits a detectable signal, e.g., that can be received by a receiver, e.g., as described in greater detail below. The signal generation component of certain embodiments can be any convenient device that is capable of producing a detectable signal and/or modulating transduced broadcast power, upon activation by the activation component. Detectable signals of interest include, but are not limited to: conductive signals, acoustic signals, etc. As reviewed above, the signals emitted by the signal generator may be generic or unique signals, where representative types of signals of interest include, but are not limited to: frequency shift coded signals; amplitude modulation signals; frequency modulation signals; etc.

In certain embodiments, the signal generation element includes circuitry, as developed in more detail below, which produces or generates the signal. The type of circuitry chosen may depend, at least in part, on the driving power that is supplied by the power source of the identifier. For example, where the driving power is 1.2 volts or above, standard CMOS circuitry may be employed. In other embodiments where the driving power ranges from about 0.7 to about 1.2 V, sub-threshold circuit designs may be employed. For driving powers of about 0.7 V or less, zero-threshold transistor designs may be employed.

In certain embodiments, the signal generation component includes a voltage-controlled oscillator (VCO) that can generate a digital clock signal in response to activation by the activation component. The VCO can be controlled by a digital circuit, which is assigned an address and which can control the VCO with a control voltage. This digital control circuit can be embedded onto a chip that includes the activation component and oscillator. Using amplitude modulation or phase shift keying to encode the address, an identifying signal is transmitted.

The signal generation component may include a distinct transmitter component that serves to transmit the generated signal to a remote receiver, which may be internal or external to the patient, as reviewed in greater detail below. The transmitter component, when present, may take a number of different configurations, e.g., depending on the type of signal that is generated and is to be emitted. In certain embodiments, the transmitter component is made up of one or more electrodes. In certain embodiments, the transmitter component is made up of one or more wires, e.g., in the form of antenna(e). In certain embodiments, the transmitter component is made up of one or more coils. As such, the signal transmitter may include a variety of different transmitters, e.g., electrodes, antennas (e.g., in the form of wires) coils, etc. In certain embodiments, the signal is transmitted either by one or two electrodes or by one or two wires. A two-electrode transmitter is a dipole; a one electrode transmitter forms a monopole. In certain embodiments, the transmitter only requires one diode drop of power. In some embodiments, the transmitter unit uses an electric dipole or electric monopole antenna to transmit signals.

Figure 9:
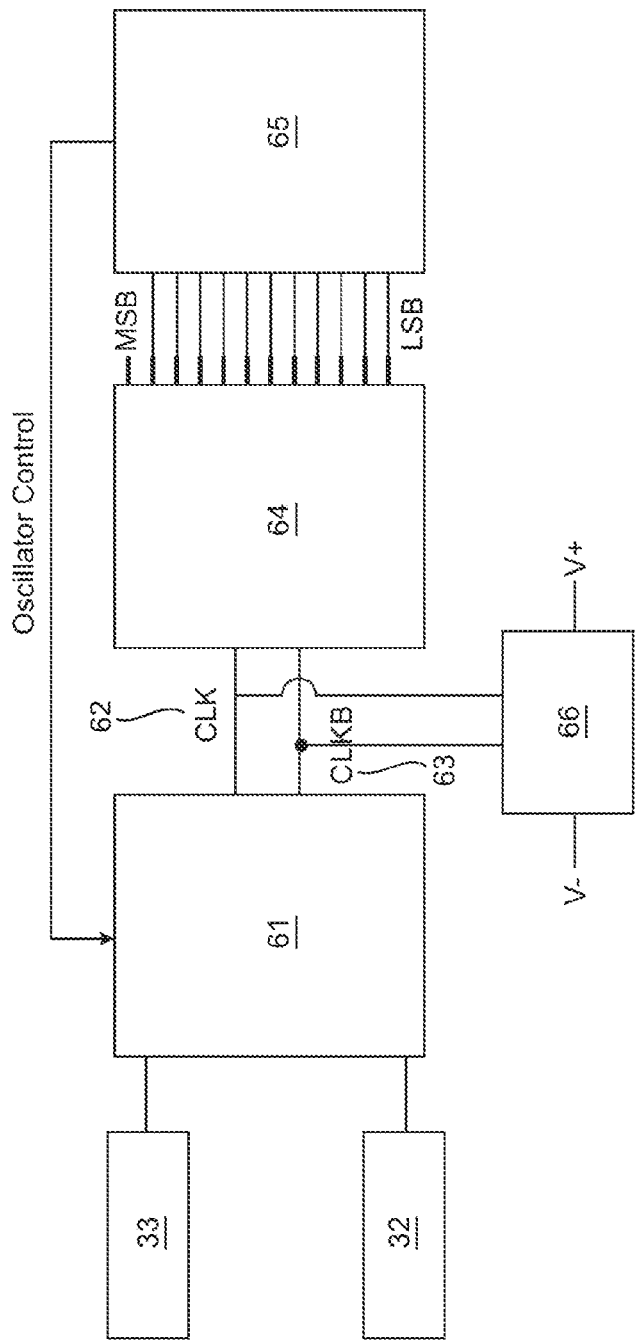
FIG. 9 provides detail of certain implementations of an electronic circuit of various embodiments of the invention.

FIG. 9 shows the detail of one implementation of an electronic circuit that can be employed in an identifier according to the present invention. On the left side are the two battery electrodes comprising a first metal (electrode 32) and a second metal (electrode 33). These metals, when in contract with an electrolyte (produced upon contact with target site fluid, either alone or in combination with dried conductive medium precursor, as reviewed above), form a battery that provides power to an oscillator 61, in this case shown as a schematic. The first metal (electrode 32) provides a low voltage, (ground) to the oscillator 61. The second metal (electrode 33) provides a high voltage ($V_{high}$) to the oscillator 61. As the oscillator 61 becomes operative, it generates a clock signal 62 and an inverted clock signal 63, which are opposites of each other. These two clock signals go into the counter 64 which simply counts the number of clock cycles and stores the count in a number of registers. In the example shown here, an 8 bit counter is employed. Thus, the output of counter 64 begins with a value of "00000000," changes to "00000001" at the first clock cycle, and continues up to "11111111." The 8-bit output of counter 64 is coupled to the input of an address multiplexer (mux) 65. In one embodiment, mux 65 contains an address interpreter, which can be hard-wired in the circuit, and generates a control voltage to control the oscillator 61. Mux 65 uses the output of counter 64 to reproduce the address in a serial bit stream, which is further fed to the signal-transmission driving circuit. Mux 65 can also be used to control the duty-cycle of the signal transmission. In one embodiment, mux 65 turns on signal transmission only one sixteenth of the time, using the clock counts generated by counter 64. Such a low duty cycle conserves power and also allows other devices to transmit without jamming their signals. The address of a given chip can be 8 bits, 16 bits or 32 bits. Typically, more than 8 bits will be used in a product because there are so many different types of pharmaceuticals. Each pharmaceutical will have its own specific address.

The present invention also allows the possibility that, where appropriate, each pharmaceutical batch can be provided with a batch specific address. This allows identification of where the pill was made, when the pill was made, and in what batch it was made. In some cases, each pill will have a unique identifier. This would be particularly useful when drugs are more likely to be subsequently stolen or used illicitly, and thus should be tracked, or where questions of contamination may arise.

According to one embodiment, mux 65 produces a control voltage, which encodes the address serially and is used to vary the output frequency of oscillator 61. By example, when the control voltage is low, that is, when the serial address bit is at a 0, a 1 megahertz signal is generated by the oscillator. When the control voltage is high, that is, when the address bit is a 1, a 2 megahertz signal is generated the oscillator. Alternately, this can be 10 megahertz and 20 megahertz, or a phase shift keying approach where the device is limited to modulating the phase. The purpose of mux 65 is to control the frequency of the oscillator or an AC alternative embodiment of the amplified signal of oscillation.

The outputs of mux 65 are coupled to electrode drive 66 which can drive the electrodes to impose a differential potential to the solution, drive an oscillating current through a coil to generate a magnetic signal, or drive a single electrode to push or pull charge to or from the solution.

In this manner, the device broadcasts the sequence of 0's and 1's which constitute the address stored in mux 65. That address would be broadcast repeatedly, and would continue broadcasting until the first metal or the second metal (32 and 33) is consumed and dissolved in the solution, when the battery no longer operates.

Figure 13:
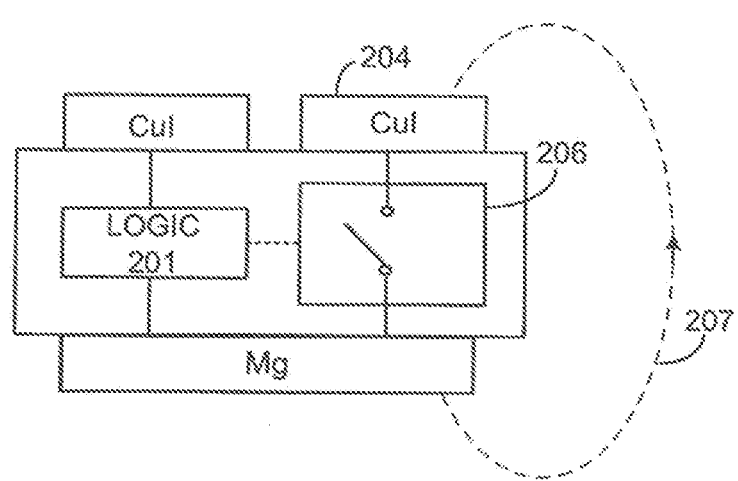
FIG. 13 shows one exemplary design of the driver circuit that uses split battery electrodes for transmission, in accordance with one embodiment of the present invention.

In a further embodiment, the device can avoid the use of separate transmission electrodes by using the battery electrodes for transmission. FIG. 13 shows an example of such a configuration. The driver circuit 206 essentially contains a switch coupled between the anode 204 and the cathode. This switch can be turned on or off by the address signal from the logic circuit 201. When the switch is turned on, the battery for the driver circuit is effectively short-circuited within the chip. Consequently, a current 207 flows through the body from the cathode to anode 204. The resistance of the body tissue can thereby generate a voltage difference, which can be readily detected by, for example, a differential amplifier.

Other configurations for the signal generation component are of course possible. Other configurations of interest include, but are not limited to: those described in copending PCT application serial no. PCT/US 2006/016370; the disclosure of which is herein incorporated by reference.

Additional Components

Depending on the particular embodiment, the identifier may include a number of different additional components. Some components of interest include, but are not limited, those reviewed below.

Deactivation Component

Where desired, the identifier may also include a deactivation mechanism that disables the identifier if the identifier is not employed as intended, e.g., the composition with which it is associated is not ingested. In certain embodiments, the identifier includes a deactivation mechanism that deactivates the identifier so that it if someone tries to turn it on in a way other than ingesting it, the identifier is deactivated and no signal can be transmitted. Deactivation mechanisms of interest may include one or more of the following components: inclusion of a light-sensitive film that destroys a component of the identifier, e.g., memory, upon exposure to light, a light sensitive battery material, e.g., that is disrupted or destroyed if exposed to light, an identifier that includes components which are sensitive to and inactivated in response to exposure to oxygen, air, moisture, etc. Inactivation of the identifier may include opening a trace, shorting a trace, reducing battery voltage, etc.

Power Enhancers

Where the activator is a power source that is turned on upon contact with a target physiological site, in certain embodiments, circuits for enhancing or boosting voltage output of the power source, e.g., battery, are provided, e.g., charge pumping circuits, charge doublers, etc. Such voltage enhancing elements may enhance the voltage output by at least about 2-fold or more, such as by about 5-fold or more.

Power Storage

In certain embodiments, the activation component includes a power storage element. For example, a duty cycle configuration may be employed, e.g., where slow energy production from a battery is stored in a power storage element, e.g., in a capacitor, which then provides a burst of power that is deployed to the signal generation component. In certain embodiments, the activation component includes a timing element which modulates, e.g., delays, delivery of power to the signal generation element, e.g., so signals from different compositions, e.g., pills, that are administered at substantially the same time are produced at different times and are therefore distinguishable.

Additional Features

In certain embodiments, the compositions are characterized by having one or more of the following features. In certain embodiments, the compositions include an identifier which employs a conductive near-field mode of communication in which the body itself is employed as a conductive medium. In such embodiments, the compositions include circuitry that, when freed from the composition upon disruption of the composition (e.g., as described above) the circuitry comes into direct contact with the body and does not remain encapsulated or protected in some manner. In these embodiments, the signal is not a magnetic signal or high frequency (RF) signal. In certain embodiments, the systems are ones that include a receiver which is stably associated with the body, e.g., implanted or topically applied to an external location, such that the systems are distinguished from those in which an external device that is not stably associated with the body is employed to collect data. In certain embodiments, the compositions do not include an imaging system, e.g., camera or other visualization or imaging element, or components thereof, e.g., CCD element, illumination element, etc. In certain embodiments, the compositions do not include a sensing element, e.g., for sensing a physiological parameter, beyond the activator which detects contact with the targeted physiological site. In certain embodiments, the compositions do not include a propulsion element. In certain embodiments, the compositions do not include a sampling element, such as a fluid retrieval element. In certain embodiments, the compositions do not include an actuatable active agent delivery element, such as an element that retains an active agent with the composition until a signal is received that causes the delivery element to release the active agent.

Active Agent Component

Certain embodiments of the subject compositions include an active agent component. "Active agent" includes any compound or mixture of compounds which produces a physiological result, e.g., a beneficial or useful result, upon contact with a living organism, e.g., a mammal, such as a human. Active agents are distinguishable from such components as vehicles, carriers, diluents, lubricants, binders and other formulating aids, and encapsulating or otherwise protective components. The active agent may be any molecule, as well as binding portion or fragment thereof, that is capable of modulating a biological process in a living subject. In certain embodiments, the active agent may be a substance used in the diagnosis, treatment, or prevention of a disease or as a component of a medication. In certain embodiments, the active agent may be a chemical substance, such as a narcotic or hallucinogen, which affects the central nervous system and causes changes in behavior. Active agents of interest include those listed in PCT application serial no. PCT/US 2006/016370; the disclosure of which list is herein incorporated by reference. Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; etc. The active agent of the compositions are typically present in a pharmaceutically acceptable vehicle or carrier, e.g., as described below. In certain embodiments, the active agent is present in an amount of from about 0.1% to about 90% by weight, e.g., from about 1% to about 30% by weight of the active compound.

Pharmaceutically Acceptable Carrier

Where desired, the compositions of the invention may include a pharmaceutically acceptable vehicle (i.e., carrier). Common carriers and excipients, such as corn starch or gelatin, lactose, dextrose, sucrose, microcrystalline cellulose, kaolin, mannitol, dicalcium phosphate, sodium chloride, and alginic acid are of interest. Disintegrators commonly used in the formulations of the invention include croscarmellose, microcrystalline cellulose, corn starch, sodium starch glycolate and alginic acid.

A liquid composition may comprise a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder. For example, a powder containing active compound, suspending agent, sucrose and a sweetener can be reconstituted with water to form a suspension; and a syrup can be prepared from a powder containing active ingredient, sucrose and a sweetener.

A composition in the form of a tablet or pill can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

"Controlled release", "sustained release", and similar terms are used to denote a mode of active agent delivery that occurs when the active agent is released from the delivery vehicle at an ascertainable and controllable rate over a period of time, rather than dispersed immediately upon application or injection. Controlled or sustained release may extend for hours, days or months, and may vary as a function of numerous factors. For the pharmaceutical composition of the present invention, the rate of release will depend on the type of the excipient selected and the concentration of the excipient in the composition. Another determinant of the rate of release is the rate of hydrolysis of the linkages between and within the units of the polyorthoester. The rate of hydrolysis in turn may be controlled by the composition of the polyorthoester and the number of hydrolysable bonds in the polyorthoester. Other factors determining the rate of release of an active agent from the present pharmaceutical composition include particle size, acidity of the medium (either internal or external to the matrix) and physical and chemical properties of the active agent in the matrix.

As such, an active pharmaceutical agent can be placed within any controlled-release structure (e.g. a gastroretentive formulation, enteric formulations, timed-release formulations, colonic formulation). Thus the identifier becomes active at the same time that the active ingredient is released. Further, more than one identifier can be incorporated into a controlled release structure, e.g. two identifiers, one of which activates at the start of the controlled release and the second in the middle or at the end.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

Other components suitable for use in the formulations of the present invention can be found in Remington's Pharmaceutical Sciences, Mace Publishing Company, Philadelphia, Pa., 17th ed. (1985).

Identifier Fabrication

In certain embodiments of interest, the identifier element includes a semiconductor support component. Any of a variety of different protocols may be employed in manufacturing the identifier structures and components thereof. For example, molding, deposition and material removal, e.g., planar processing techniques, such as Micro-Electro-Mechanical Systems (MEMS) fabrication techniques, including surface micromachining and bulk micromachining techniques, may be employed. Deposition techniques that may be employed in certain embodiments of fabricating the structures include, but are not limited to: electroplating, cathodic arc deposition, plasma spray, sputtering, e-beam evaporation, physical vapor deposition, chemical vapor deposition, plasma enhanced chemical vapor deposition, etc. Material removal techniques included, but are not limited to: reactive ion etching, anisotropic chemical etching, isotropic chemical etching, planarization, e.g., via chemical mechanical polishing, laser ablation, electronic discharge machining (EDM), etc. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner. Illustrative fabrication methods of interest are described in greater detail in PCT application serial no. PCT/US 2006/16370 titled "Pharma-Informatics System" and filed on Apr. 28, 2006 and published as WO 2006/116718; the disclosure of which is herein incorporated by reference.

Methods of Making Compositions

Figure 11:
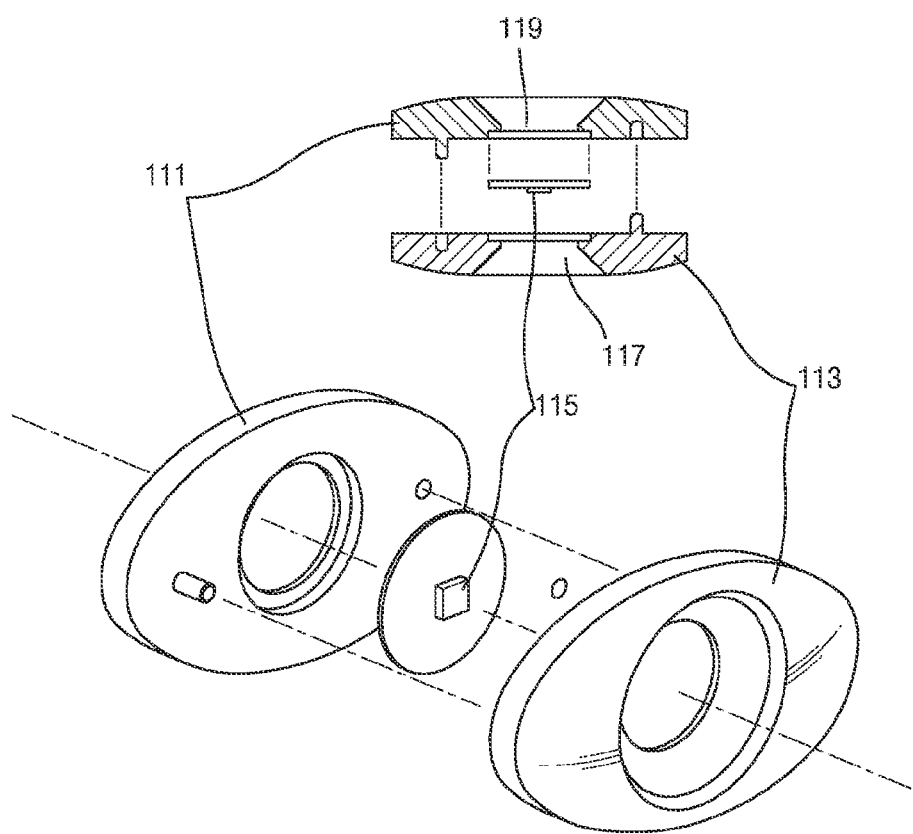
FIG. 11 provides two views of an open faced table format according to an embodiment of the invention.

A variety of manufacturing protocols may be employed to produce compositions according to the invention. In manufacturing the subject compositions, a signal generation element is stably associated with a carrier composition, e.g., pharmaceutical dosage composition, in some manner. By stably associated is meant that the signal generation element and the dosage form are not separate from each other, at least until administered to the subject in need thereof, e.g., by ingestion. The signal generation element may be stably associated with the pharmaceutical carrier/active agent component of the composition in a number of different ways. In certain embodiments, where the carrier/active agent component is a solid structure, e.g., such as a tablet or pill, the carrier/active agent component is produced in a manner that provides a cavity for the signal generation element. The signal generation element is then placed into the cavity and the cavity sealed, e.g., with a biocompatible material, to produce the final composition. For example, in certain embodiments a tablet is produced with a die that includes a feature which produces a cavity in the resultant compressed tablet. The signal generation element is placed into the cavity and the cavity sealed to produce the final tablet. In a variation of this embodiment, the tablet is compressed with a removable element, e.g., in the shape of a rod or other convenient shape. The removable element is then removed to produce a cavity in the tablet. The signal generation element is placed into the cavity and the cavity sealed to produce the final tablet. In another variation of this embodiment, a tablet without any cavity is first produced and then a cavity is produced in the tablet, e.g., by laser drilling. The signal generation element is placed into the cavity and the cavity sealed to produce the final tablet. In yet other tablet embodiments, an open face pharmaceutical carrier/active agent tablet configuration (e.g., as shown in FIG. 11) is employed, where the active agent/carrier is first prepared into an annular tablet format that includes a circular opening. For example, in the embodiment shown in FIG. 11, two open annular format pharmaceutical compositions 111 and 113 are prepared, e.g., by pressing, or other convenient fabrication protocol. Also shown is identifier 115. Following production of the annular tablets 111 and 113, the identifier is positioned in the opening, as shown. The remaining openings 117 and 119 are then filled or covered with any of the activating films described above (not shown). In yet other embodiments, a tablet is produced by combining the signal generation element with subparts of the tablet, where the subparts may be pre-made subparts or manufactured sequentially. For example, in certain embodiments tablets are produced by first making a bottom half of the tablet, placing the signal generation element on a location of the bottom half of the tablet, and then placing top portion of the tablet over the bottom half and signal generation element to produce the final desired composition. In certain embodiments, a tablet is produced around a signal generation element such that the signal generation element is located inside of the produced tablet. For example, a signal generation element, which may or may not be encapsulated in a biocompatible compliant material, e.g., gelatin (to protect the signal generation element), is combined with carrier/active agent precursor, e.g., powder, and compressed or molded into a tablet in a manner such that the signal generation element is located at an internal position of the tablet. Instead of molding or compressing, the carrier/active agent component is, in certain embodiments, sprayed onto the signal generation element in a manner that builds up the tablet structure. In yet another embodiment, the active agent/carrier component precursor may be a liquid formulation which is combined with the signal generation element and then solidified to produce the final composition. In yet other embodiments, pre-made tablets may be fitted with the signal generation element by stably attaching the signal generation element to the tablet. Of interest are protocols that do not alter the properties of the tablet, e.g., dissolution etc. For example, a gelatin element that snap fits onto one end of a tablet and has the chip integrated with it is employed in certain embodiments. The gelatin element is colored in certain embodiments to readily identify tablets that have been fitted with the signal generation element. Where the composition has an active agent/carrier composition filled capsule configuration, e.g., such as a gelatin capsule filled configuration, the signal generation element may be integrated with a capsule component, e.g., top or bottom capsule, and the capsule filled with the active agent/carrier composition to produce the final composition. The above reviewed methods of manufacture are merely illustrative of the variety of different ways in which the compositions of the invention may be manufactured.

Systems

Also provided are systems that include the subject compositions. Systems of the subject invention include, in certain embodiments, one or more controlled activation identifiers, e.g., as reviewed above, as well as a signal detection component, e.g., in the form of a receiver. The signal detection component may vary significantly depending on the nature of the signal that is generated by the signal generation element of the composition, e.g., as reviewed above.

In certain embodiments, the signal detection component is an implantable component. By implantable component is meant that the signal detection component is designed, i.e., configured, for implantation into a subject, e.g., on a semi-permanent or permanent basis. In these embodiments, the signal detection component is in vivo during use. In yet other embodiments, the signal detection component is ex vivo, by which is meant that the detection component is present outside of the body during use. In certain of these embodiments, as developed in greater detail below, either separate from or integrated with the ex vivo detection component may be a dosage dispenser element, e.g., for dispensing dosages of the compositions based on signal detected from the signal generation element of the detector. Such features may also be present in implantable detection components, e.g., to provide a closed loop administration system that administers a subsequent dosage based on input about ingestion of a previous dosage.

As reviewed above, in certain embodiments the signal generation element of the composition is activated upon contact with a target body site. In certain of these embodiments, the signal detection component is activated upon detection of a signal from the signal generation element. In certain of these embodiments, the composition generates an intermittent signal. In certain of these embodiments, the detection element is capable of simultaneously detecting multiple compositions.

Signal receivers for use in the invention are further described in PCT application serial no. PCT/US 2006/16370 titled "Pharma-Informatics System" and filed on Apr. 28, 2006 and published as WO 2006/116718, as well as provisional application Ser. No. 60/887,780 titled "Signal Receivers for Pharma-Informatics Systems," and filed on Feb. 1, 2007; 60/949,223 titled "Ingestible Even Marker," and filed on Jul. 11, 2007 and 60/956,694 titled "Personal Health Signal Receivers," and filed on Aug. 18, 2007; the disclosures of which are herein incorporated by reference.

Figure 10:
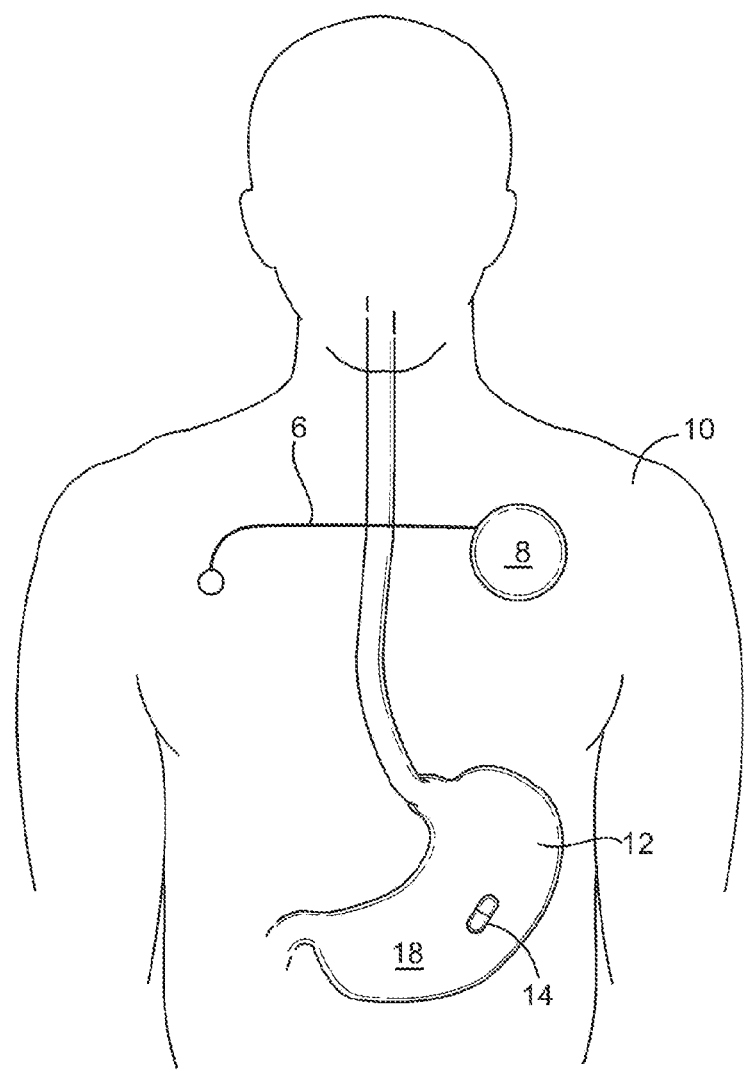
FIG. 10 provides a diagrammatic, exemplary representa- tion of the pill embodiment as part of system, in accordance with the present invention.

In certain embodiments, the signal detection component includes a cardiac monitoring element, such as shown in the system of FIG. 10. FIG. 10 provides a diagrammatic, exemplary representation of a pill/capsule embodiment of the present invention, in which the composition is configured as an orally ingestible pharmaceutical formulation in the form of a pill or capsule. The stomach 12 of the patient 10 who ingests the composition 14 is shown. This "smart pill" is shown as it has traveled from the mouth 16 to inside 18 the patient's stomach. Upon reaching the stomach, the pill/capsule undergoes a dissolving process with both the mechanical action of the stomach and the various chemical materials in the stomach fluids, such as hydrochloric acid and other digestive agents. FIG. 10 also shows an implanted cardiovascular device "can" 8 and a lead 6, which components are employed to monitor and detect the signal emitted from pill 14. The monitoring device can be positioned in other locations as well, such as subcutaneously, in the heart, or in the waist near the stomach, for example. Positioning may be suggested by a particular application.

Methods

Controlled activation identifiers of the invention find use in a variety of different applications, including delivery of pharmaceutical agents, in diagnostic and monitoring applications, etc. In methods where the identifiers are employed in compositions that include one or more pharmaceutically active agents, an effective amount of a composition of the invention is administered to a subject in need of the active agent present in the composition, where "effective amount" means a dosage sufficient to produce the desired result, e.g., an improvement in a disease condition or the symptoms associated therewith, the accomplishment of a desired physiological change, etc. The amount that is administered may also be viewed as a therapeutically effective amount. A "therapeutically effective amount" means the amount that, when administered to a subject for treating a disease, is sufficient to effect treatment for that disease.

The composition may be administered to the subject using any convenient means capable of producing the desired result, where the administration route depends, at least in part, on the particular format of the composition, e.g., as reviewed above. As reviewed above, the compositions can be formatted into a variety of formulations for therapeutic administration, including but not limited to solid, semi solid or liquid, such as tablets, capsules, powders, granules, ointments, solutions, suppositories and injections. As such, administration of the compositions can be achieved in various ways, including, but not limited to: oral, buccal, rectal, parenteral, intraperitoneal, intradermal, transdermal, intracheal, etc., administration. In pharmaceutical dosage forms, a given composition may be administered alone or in combination with other pharmaceutically active compounds, e.g., which may also be compositions having signal generation elements stably associated therewith.

The subject methods find use in the treatment of a variety of different conditions, including disease conditions. The specific disease conditions treatable by with the subject compositions are as varied as the types of active agents that can be present in the subject compositions. Thus, disease conditions include, but are not limited to: cardiovascular diseases, cellular proliferative diseases, such as neoplastic diseases, autoimmune diseases, hormonal abnormality diseases, infectious diseases, pain management, and the like.

By treatment is meant at least an amelioration of the symptoms associated with the disease condition afflicting the subject, where amelioration is used in a broad sense to refer to at least a reduction in the magnitude of a parameter, e.g. symptom, associated with the pathological condition being treated. As such, treatment also includes situations where the pathological condition, or at least symptoms associated therewith, are completely inhibited, e.g. prevented from happening, or stopped, e.g. terminated, such that the subject no longer suffers from the pathological condition, or at least the symptoms that characterize the pathological condition. Accordingly, "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes pain.

A variety of subjects are treatable according to the present methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In representative embodiments, the subjects will be humans.

In certain embodiments, the subject methods, as described above, are methods of managing a disease condition, e.g., over an extended period of time, such as 1 week or longer, 1 month or longer, 6 months or longer, 1 year or longer, 2 years or longer, 5 years or longer, etc. The subject methods may be employed in conjunction with one or more additional disease management protocols, e.g., electrostimulation based protocols in cardiovascular disease management, such as pacing protocols, cardiac resynchronization protocols, etc; lifestyle, such a diet and/or exercise regimens for a variety of different disease conditions; etc.

In certain embodiments, the methods include modulating a therapeutic regimen based data obtained from the compositions. For example, data may be obtained which includes information about patient compliance with a prescribed therapeutic regimen. This data, with or without additional physiological data, e.g., obtained using one or more sensors, such as the sensor devices described above, may be employed, e.g., with appropriate decision tools as desired, to make determinations of whether a given treatment regimen should be maintained or modified in some way, e.g., by modification of a medication regimen and/or implant activity regimen. As such, methods of invention include methods in which a therapeutic regimen is modified based on signals obtained from the composition(s).

In certain embodiments, also provided are methods of determining the history of a composition of the invention, where the composition includes an active agent, an identifier element and a pharmaceutically acceptable carrier. In certain embodiments where the identifier emits a signal in response to an interrogation, the identifier is interrogate, e.g., by a wand or other suitable interrogation device, to obtain a signal. The obtained signal is then employed to determine historical information about the composition, e.g., source, chain of custody, etc.

In yet other embodiments where the identifier is one that survives digestion, the methods generally include obtaining the signal generation element of the composition, e.g., by retrieving it from a subject that has ingested the composition, and then determining the history of the composition from obtained signal generation element. For example, where the signal generation element includes an engraved identifier, e.g., barcode or other type of identifier, the engraved identifier may be retrieved from a subject that has ingested the composition and then read to identify at least some aspect of the history of the composition, such as last known purchaser, additional purchasers in the chain of custody of the composition, manufacturer, handling history, etc. In certain embodiments, this determining step may include accessing a database or analogous compilation of stored history for the composition.

The present invention provides the clinician an important new tool in their therapeutic armamentarium: automatic detection and identification of pharmaceutical agents actually delivered into the body. The applications of this new information device and system are multi-fold. Applications include, but are not limited to: (1) monitoring patient compliance with prescribed therapeutic regimens; (2) tailoring therapeutic regimens based on patient compliance; (3) monitoring patient compliance in clinical trials; (4) monitoring usage of controlled substances; and the like. Each of these different illustrative applications is reviewed in greater detail below in PCT/US 2006/16370 titled "Pharma-Informatics System" and filed on Apr. 28, 2006 and published as WO 2006/116718; the disclosure of which is herein incorporated by reference.

Also of interest are methods in which the identifier is ingested apart from any pharmaceutical agent. Such methods include those in which the identifier is employed as an ingestible event marker. In such methods, the identifier is ingested without a pharmaceutically active agent. The identifier may be ingested in a pharmaceutically acceptable vehicle, e.g., as described above. Specific applications in which the identifier is employed as an ingestible event marker include, but are not limited to, those described in U.S. Provisional Application Ser. No. 60/949,223 titled "Ingestible Event Marker," and filed on Jul. 11, 2007; the disclosures of which are herein incorporated by reference.

One example of a specific application in which the controlled activation identifier is not administered with an active agent and is instead employed as an ingestible event marker is the application of monitoring GI tract motility. In such applications, a controlled activation device that activates only at high pH is employed to determine the transit time from ingestion to the small intestine. In a variation of this embodiment, multiple devices that activate in different parts of the GI tract are employed, where this embodiment may be used for mapping the residence time of the device in various parts of the GI tract. For example, in one instance three controlled activation identifiers (which may be present in the same pill or separate pills) are employed. The first identifier is configured to activate immediately upon ingestion (e.g., which it reaches the stomach). The second controlled activation identifier includes a low pH-insoluble, high-pH soluble coating (e.g., Eudragit) that delays activation until the identifier reaches the small intestine. The third identifier includes a controlled activation element a coating (e.g., amylase+ethyl cellulose) that is only soluble in the colon. From the activation time of the various identifiers one can determine or measure the transition time to the stomach, small intestine, and colon, and thereby gain a detailed data collection of the subject's gastrointestinal motility.

Kits

Also provided are kits for practicing the subject methods. Kits may include one or more compositions of the invention, as described above. The dosage amount of the one or more pharmacological agents provided in a kit may be sufficient for a single application or for multiple applications. Accordingly, in certain embodiments of the subject kits a single dosage amount of a pharmacological agent is present and in certain other embodiments multiple dosage amounts of a pharmacological agent may be present in a kit. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent. Suitable means for delivering one or more pharmacological agents to a subject may also be provided in a subject kit. In certain embodiments the kits may also include a signal receiving element, as reviewed above. In certain embodiments, the kits may also include an external monitor device, e.g., as described above, which may provide for communication with a remote location, e.g., a doctor's office, a central facility etc., which obtains and processes data obtained about the usage of the composition.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A pharmaceutical composition comprising:
   a pharmaceutical active agent;
   a controlled activation identifier that transmits a signal upon contact with a target site of a body, wherein the signal is a conductive signal and wherein the controlled activation identifier comprises first and second electrodes that are configured to create a voltaic cell when in contact with a conducting fluid at the target site, wherein the voltaic cell supplies power to the controlled activation identifier, and wherein the controlled activation identifier is configured to transmit the conductive signal through tissue of to the body upon the first and second electrodes contacting the conducting fluid at the target site and the voltaic cell supplying power to the controlled activation identifier; and
   a pharmaceutically acceptable carrier.

2. The pharmaceutical composition of claim 1, wherein the first and second electrodes transmit the conductive signal.

3. A controlled activation ingestible identifier that transmits a signal upon contact with a conducting fluid present at a target site of a body, wherein the signal is a conductive signal and wherein the controlled activation identifier comprises first and second electrodes that are configured to create a voltaic cell when in contact with the conducting fluid at the target site, wherein the voltaic cell supplies power to the controlled activation identifier, and wherein the controlled activation identifier is configured to transmit the conductive signal through tissue of the body upon the first and second electrodes contacting the conducting fluid at the target site and the voltaic cell supplying power to the controlled activation identifier.

4. The controlled activation ingestible identifier according to claim 3, wherein the identifier comprises: a solid support; wherein the first and second electrodes comprise first and second materials with dissimilar electrochemical activities and wherein the electrodes are present on a surface of the solid support.

5. The controlled activation ingestible identifier according to claim 4, wherein the identifier further comprises a dried conductive medium precursor.

6. The controlled activation ingestible identifier according to claim 5, wherein the identifier further comprises a protective barrier that retains the dried conductive medium precursor.

7. The controlled activation ingestible identifier according to claim 4, wherein the identifier further comprises a protective barrier.

8. The controlled activation ingestible identifier according to claim 7, wherein the protective barrier is a semipermeable membrane.

9. The controlled activation ingestible identifier according to claim 7 wherein the protective barrier is a solid barrier comprising a flow path.

10. The controlled activation ingestible identifier according to claim 9, wherein the flow path is a capillary flow path.

11. The controlled activation ingestible identifier according to claim 10, wherein the capillary flow path comprises at least one surface that has been surface energy modified to enhance hydrophilic fluid flow through the capillary flow path.

12. The controlled activation ingestible identifier according to claim 4, wherein the identifier is protected by a barrier that disrupts upon contact with a fluid having sufficient conductivity to activate the identifier in a predetermined manner.

13. The controlled activation ingestible identifier according to claim 4, wherein the identifier is protected by a polymeric coating that dissolves upon contact with a fluid in a time-delayed manner.

14. The controlled activation ingestible identifier according to claim 4, wherein the identifier further comprises a signal producing system that transmits a signal when the dried conductive medium precursor is combined with water to produce a conductive medium that conductively couples the first and second materials.

15. The controlled activation ingestible identifier according to claim 3, wherein the first and second electrodes transmit the conductive signal.

16. A system comprising:
   a controlled activation ingestible identifier that transmits a signal upon contact with a conducting fluid present at a target site of a body, wherein the signal is a conductive signal and wherein the controlled activation identifier comprises first and second electrodes that are configured to create a voltaic cell when in contact with the conducting fluid at the target site, wherein the voltaic cell supplies power to the controlled activation identifier, and wherein the controlled activation identifier is configured to transmit the conductive signal through tissue of the body upon the first and second electrodes contacting the conducting fluid at the target site and the voltaic cell supplying power to the controlled activation identifier; and
   a receiver for detecting a signal produced by the identifier.

17. The system according to claim 16, wherein the receiver is an in vivo receiver.

18. The system according claim 16, wherein the receiver is an ex vivo receiver.

19. The system according claim 16, wherein the first and second electrodes transmit the conductive signal.

20. A method comprising:
   administering to a subject a controlled activation ingestible identifier that transmits a signal upon contact with a conducting fluid present at a target site, wherein the controlled activation identifier comprises first and second electrodes that are configured to create a voltaic cell when in contact with the conducting fluid at the target site, wherein the voltaic cell is configured to supply power to the controlled activation identifier, and wherein the controlled activation identifier is configured to transmit the signal through tissue of the body upon the first and second electrodes contacting the conducting fluid at the target site and the voltaic cell supplying power to the controlled activation identifier, wherein the signal is a conductive signal transmitted to a body with first and second electrodes; and transmitting, by the controlled activation identifier, the conductive signal upon contact with the target site of a body.

21. The method of claim 20, wherein the first and second electrodes transmit the conductive signal.

* * * * *